(12) United States Patent
Bake et al.

(10) Patent No.: US 12,232,966 B2
(45) Date of Patent: Feb. 25, 2025

(54) METHOD OF DESIGNING AND POSITIONING A MEDICAL IMPLANT AND AN IMPLANT COMPRISING A POSITIONING MARK

(71) Applicant: EPISURF IP-MANAGEMENT AB, Stockholm (SE)

(72) Inventors: Nina Bake, Lidingö (SE); Maria Kroll, Jönköping (SE); Niklas Hero, Bankeryd (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 450 days.

(21) Appl. No.: 17/565,692

(22) Filed: Dec. 30, 2021

(65) Prior Publication Data

US 2022/0117743 A1 Apr. 21, 2022

Related U.S. Application Data

(60) Division of application No. 16/379,076, filed on Apr. 9, 2019, now abandoned, which is a
(Continued)

(51) Int. Cl.
*A61F 2/30* (2006.01)
*A61B 17/16* (2006.01)
(Continued)

(52) U.S. Cl.
CPC ...... *A61F 2/30942* (2013.01); *A61B 17/1615* (2013.01); *A61B 17/1637* (2013.01);
(Continued)

(58) Field of Classification Search
CPC ...... A61F 2/4618; A61F 2/30756–2002/30766
See application file for complete search history.

(56) References Cited

U.S. PATENT DOCUMENTS 5,507,824 A 4/1996 Lennox
5,632,745 A * 5/1997 Schwartz ............... A61L 27/58
606/77
(Continued)

FOREIGN PATENT DOCUMENTS

EP 1 129 675 A2 9/2001
EP 1 234 555 A2 8/2002
(Continued)

OTHER PUBLICATIONS

Partial European search report issued in European patent application No. 19200903.3, dated Jan. 27, 2020.

*Primary Examiner* — Zade Coley
(74) *Attorney, Agent, or Firm* — MEDLER FERRO WOODHOUSE & MILLS PLLC

(57) ABSTRACT

The present invention relates to a method for designing an implant comprising designing a contour curvature of the implant so that an articulating surface of the implant is designed to correspond to a simulated healthy articulating surface of a damaged articulating surface of a joint. The implant is provided with at least one positioning mark
(Continued)

designed to be used for determining the orientation in which the implant is to be placed in a recess made in a damaged articulating surface of a joint. Further, the present invention relates to methods for positioning and inserting a medical implant in a recess.

6 Claims, 17 Drawing Sheets

Related U.S. Application Data continuation-in-part of application No. 16/148,134, filed on Oct. 1, 2018, now Pat. No. 11,123,194, which is a division of application No. 14/784,376, filed as application No. PCT/EP2013/057847 on Apr. 15, 2013, now Pat. No. 10,143,556.

(51) Int. Cl.
| | | |
|---|---|---|
| *A61B 17/17* | (2006.01) | |
| *A61B 90/00* | (2016.01) | |
| *A61F 2/46* | (2006.01) | |
| *A61B 17/00* | (2006.01) | |
| *A61B 17/56* | (2006.01) | |
| *A61B 34/10* | (2016.01) | |
| *A61F 2/38* | (2006.01) | |

(52) U.S. Cl.
CPC .......... *A61B 17/1764* (2013.01); *A61B 90/03* (2016.02); *A61B 90/06* (2016.02); *A61F 2/30756* (2013.01); *A61F 2/4618* (2013.01); *A61F 2/4684* (2013.01); *A61B 2017/0046* (2013.01); *A61B 17/1675* (2013.01); *A61B 2017/568* (2013.01); *A61B 2034/108* (2016.02); *A61B 2090/034* (2016.02); *A61B 2090/036* (2016.02); *A61B 2090/037* (2016.02); *A61B 2090/062* (2016.02); *A61F 2002/30617* (2013.01); *A61F 2002/30759* (2013.01); *A61F 2002/30948* (2013.01); *A61F 2002/30952* (2013.01); *A61F 2/3859* (2013.01); *A61F 2002/4662* (2013.01); *A61F 2002/4681* (2013.01); *A61F 2002/4687* (2013.01)

(56) References Cited

U.S. PATENT DOCUMENTS

| | | |
|---|---|---|
| 6,821,300 B2 | 11/2004 | Masini |
| 8,137,356 B2 | 3/2012 | Hestad et al. |
| 10,143,556 B2 | 12/2018 | Bake et al. |
| 11,123,194 B2 | 9/2021 | Bake et al. |
| 2004/0148030 A1 | 7/2004 | Ek |
| 2005/0288676 A1 | 12/2005 | Schnieders et al. |
| 2006/0030853 A1 | 2/2006 | Haines |
| 2006/0149390 A1 | 7/2006 | Long et al. |
| 2006/0247790 A1* | 11/2006 | McKay .............. A61F 2/30756 623/23.63 |
| 2008/0243127 A1 | 10/2008 | Lang et al. |
| 2008/0281330 A1 | 11/2008 | Ferrante et al. |
| 2009/0131986 A1 | 5/2009 | Lee et al. |
| 2009/0319053 A1 | 12/2009 | Chu |
| 2010/0168803 A1 | 7/2010 | Hestad et al. |
| 2010/0249938 A1* | 9/2010 | Gunther ................ A61B 17/86 623/19.11 |
| 2011/0295104 A1 | 12/2011 | Teitelbaum et al. |
| 2013/0184820 A1* | 7/2013 | Schwartz ............. A61F 2/4684 623/14.12 |
| 2016/0030183 A1* | 2/2016 | Bake .................. A61B 17/1637 606/86 R |
| 2017/0156890 A1* | 6/2017 | Bake .................. A61F 2/30756 |
| 2017/0172747 A1* | 6/2017 | Bake ........................ A61F 2/38 |
| 2019/0091028 A1 | 3/2019 | Bake et al. |
| 2019/0231538 A1 | 8/2019 | Bake et al. |
| 2021/0322174 A1 | 10/2021 | Bake et al. |

FOREIGN PATENT DOCUMENTS

| | | | |
|---|---|---|---|
| EP | 1 277 450 A2 | 1/2003 | |
| EP | 1 366 718 A2 | 12/2003 | |
| EP | 2389905 A1 | 11/2011 | |
| EP | 2564792 A1 | 3/2013 | |
| WO | WO-03/007839 A2 | 1/2003 | |
| WO | WO-2009108591 A1 * | 9/2009 | ......... A61B 17/1615 |
| WO | WO-2011/080260 A1 | 7/2011 | |
| WO | WO-2013/181684 A1 | 12/2013 | |
| WO | WO-2016004991 A1 * | 1/2016 | ......... A61F 2/30756 |

\* cited by examiner

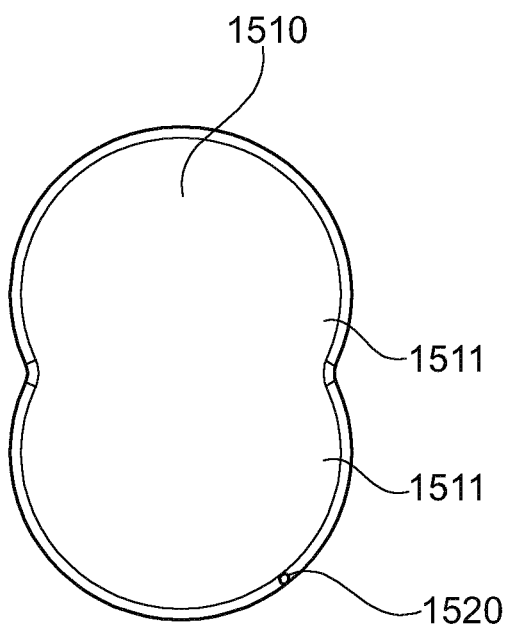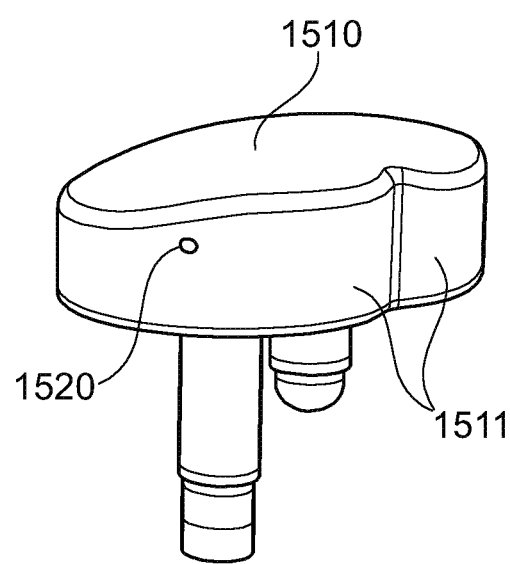
Fig. 15a
Fig. 15b

METHOD OF DESIGNING AND POSITIONING A MEDICAL IMPLANT AND AN IMPLANT COMPRISING A POSITIONING MARK

CROSS-REFERENCE TO RELATED APPLICATIONS

This application is a divisional application of co-pending prior U.S. patent application Ser. No. 16/379,076, filed Apr. 9, 2019, continuation-in-part of co-pending prior U.S. patent application Ser. No. 16/148,134, filed Oct. 1, 2018, now U.S. Pat. No. 11,123,194, issued Sep. 21, 2021, which is a divisional application of co-pending prior U.S. patent application Ser. No. 14/784,376, filed Oct. 14, 2015, now U.S. Pat. No. 10,143,556, issued Dec. 4, 2018, which is the National Stage of International Application No. PCT/EP2013/057847, filed Apr. 15, 2013. The contents of each of these applications are incorporated herein in their entirety.

FIELD OF THE INVENTION

This invention relates in general to the field of designing tools for use during replacement of damaged cartilage in an articulating surface in a joint all comprising positioning marks. The present invention also confers to tools made using the design method according to the invention and methods for rotationally positioning and inserting a medical implant in a recess.

BACKGROUND

General Background

Pain and overuse disorders of the joints in the body is a common problem. The weight-bearing and articulating surfaces of the knees, and of other joints, are covered with a layer of soft tissue that typically comprises a significant amount of hyaline cartilage. The friction between the cartilage and the surrounding parts of the joint is very low, which facilitates movement of the joints under high pressure. The cartilage is however prone to damage due to disease, injury or chronic wear. Moreover it does not readily heal after damages, as opposed to other connective tissue, and if healed the durable hyaline cartilage is often replaced by less durable fibrocartilage. This means that damages of the cartilage gradually become worse. Along with injury/disease comes a problem with pain which results in handicap and loss of function. It is therefore important to have efficient means and methods for repairing damaged cartilage in knee joints.

The advantages of implants have stimulated a further development of smaller implants that can be implanted with less invasive surgery. In this development there has also been an effort to achieve small joint implants, suitable for repair of a small cartilage injury that have a minimal influence on the surrounding parts of the joint. In the surgical operation of implanting such small implants it is critical that the implant is positioned in a precise manner. If the implant is offset from its intended position it may cause an increased wear or load on the joint. For example, if the implant is tilted this may result in an edge that projects above the cartilage surface and causes wear on the opposing cartilage in the joint. Another example is the case that the implant is placed in a too shallow position, which may result in a too high top of the implant that causes the joint to articulate in an uneven manner and increase the load on an opposing point of the joint. For the patient, also small misplacements or deviations from an ideal position may result in pain, longer time for convalescence or even a surgical operation being done in vain and making it more difficult to repair the damage in the joint. A large burden is therefore placed on the surgeon not to misplace or misfit the implant. There is therefore a need for well fitting implants as well as tools that are designed to relieve and support the surgeon in the implant surgery.

Specific Background

The design of the implant and the surgical tools, in other words, the design of the surgical kit is crucial for the outcome of the implants life-time in a joint. Also, the parameters for designing are of uttermost importance for the result in these operations. Small differences in the design can make a huge difference in fit and life-time of an implant in the body, convalescence time for the patient, economic values due to surgery time, success of operations, also the number of successful operations will increase and the working conditions for the surgeon will be improved if the designing parameters are selected right etc.

There is a need for a design method for a guide for use during repair of a cartilage damage which is more user friendly for the surgeon than the guide tools known from prior art. There is a need for a guide tool which allows for small surgical cuts and also a design method which allows for producing small guide tools which still are stable and easy to use for the surgeon allowing for precise insertion of implants in a joint.

PRIOR ART

A prior art document which describe the design of an orthopedic implants and corresponding tools is for example:
EP2389905 A1 shows a design method for designing an individually designed surgical kit.

OBJECT OF THE INVENTION

The general object of the invention is to solve the problem of designing an improved guide tool for use during cartilage repair for replacing damaged cartilage and also an improved design method for designing inserts tools and also implants. The design of the guide tool and the insert tools and the implant makes the surgical operation safer and results in better fitting implants, less surgeon dependent operation procedures and faster recovery of the patients after surgery due to that the implant guide can be made smaller and neater using this design method. It is a further object of the invention to provide a solution for making the surgical operation of rotationally positioning and inserting an implant in a recess safer and more accurate by providing a positioning mark on the implant which is adapted for rotationally positioning the implant in the recess.

SUMMARY OF THE INVENTION

The object of the invention is achieved with a system for designing a guide tool and/or a surgical kit and or an implant.

The present invention relates to a method for designing an implant, comprising:
  designing a contour curvature of the implant so that an articulating surface of the implant is designed to correspond to a simulated healthy articulating surface of a damaged articulating surface of a joint;

providing at least two substantially circular shapes such that each of said substantially circular shapes is partly overlapping at least one other substantially circular shape; and providing at least one positioning mark on at least one of said at least two substantially circular shapes such that said at least one positioning mark is designed to be used for determining the orientation in which the implant is to be placed in a recess made in a damaged articulating surface of a joint.

The present invention also relates to a method for inserting an implant in a joint, comprising:

providing an implant having at least one positioning mark, wherein said at least one positioning mark is positionally adapted on the surface of the implant to be visible for detection by a vision system;

detecting, by the vision system, said at least one positioning mark in relation to at least one of at least one mark made on the side of a recess made in the articulating surface of the joint and at least one pre-determined anatomic dependent direction; and inserting the implant in the recess by directing the at least one implant positioning mark in a direction dependent on the direction of at least one of at least one mark made on the side of a recess made in the articulating surface of the joint and at least one pre-determined anatomic dependent direction, wherein said inserting is aided by said detecting by the vision system.

The present invention further relates to a method for inserting an implant in a joint, comprising:

providing an implant having at least one positioning mark, wherein said at least one positioning mark is located on the surface of the implant to be visible for detection;

providing a storage unit, e.g. a box, for storing an implant prior to inserting the implant in a recess of a human joint, wherein said storage unit comprises at least one of a mechanical recess structure and/or holding means adapted for positioning the implant in a rotationally fixed position in the storage unit, and wherein said storage unit further comprises at least one reference feature;

detecting said at least one positioning mark in relation to said at least one reference feature;

placing the implant in the storage unit by directing the at least one implant positioning mark on the surface of the implant in a specific, e.g. pre-determined, rotational direction in relation to said at least one reference feature of the storage unit;

gripping the implant in the storage unit, wherein the implant is rotationally oriented in accordance with said specific rotational direction of the at least one implant positioning mark in relation to said at least one reference feature of the storage unit;

removing the implant from the storage unit, wherein the implant is rotationally oriented in accordance with said specific rotational direction of the at least one implant positioning mark in relation to said at least one reference feature of the storage unit when removed from the storage unit; and inserting the implant in a recess made in a human joint in a correct placement orientation, wherein said correct placement orientation is determined by how the implant is rotationally positioned in said storage unit in relation to said at least one reference feature of the storage unit.

The present invention further relates to a medical implant comprising at least two substantially circular shapes where each of said substantially circular shapes is partly overlapping at least one other circular shape, and where at least one of the at least two substantially circular shapes is provided with at least one positioning mark on its surface.

In embodiments, the technology disclosed relates to a medical implant comprising at least two substantially circular shapes such that each of said circular shapes is partly overlapping at least one other circular shape, and wherein at least one of the at least substantially circular shapes is provided with at least one positioning mark on its surface, wherein the positioning mark is designed to be used for determining the orientation in which the implant is to be placed in a recess made in a joint.

In certain embodiments, the technology disclosed relates to a method for designing an implant, comprising:

designing the shape and size of the implant dependent on the size and shape of the damage in the articulating surface and dependent on the curvature of the simulated healthy contour of the articulating surface in the area substantially coinciding with the damage; and designing the positioning mark to point out the same direction, or joint axis, as at least one of a mark made, or to be made, on the side of a recess made in the articulating surface of a joint and a positioning mark on a guide tool to be used for facilitating placement of said implant in a recess of the joint.

In certain embodiments, the technology disclosed relates to a method for designing an implant, comprising:

designing a contour curvature of the implant so that an articulating surface of the implant is designed to correspond to a simulated healthy articulating surface of a damaged articulating surface of a joint, said designing of the implant comprising placing, in a virtual 3D view, at least two substantially circular shapes such that each of said circular shapes is partly overlapping at least one other circular shape; and providing at least one positioning mark on at least one of said at least two substantially circular shapes such that said at least one positioning mark is designed to be used for determining the orientation in which the implant is to be placed in a recess made in a damaged articulating surface of a joint.

In embodiments, the technology disclosed relates to a method for designing an implant, comprising:

designing a contour curvature of the implant so that an articulating surface of the implant is designed to correspond to a simulated healthy articulating surface of a damaged articulating surface of a joint, said designing of the implant comprising placing, in a virtual 3D view, at least two substantially circular shapes such that each of said circular shapes is partly overlapping at least one other circular shape in that the combined area of the circular shapes is designed to cover, or partly cover, a damaged area; and providing at least one positioning mark on at least one of said at least two substantially circular shapes such that said at least one positioning mark is designed to be used for determining the orientation in which the implant is to be placed in a recess made in a damaged articulating surface of a joint.

In embodiments, the technology disclosed relates to a design method comprising the (further) steps of:

designing the shape and size of the implant dependent on the size and shape of the damage in the articulating surface and dependent on the curvature of the simulated healthy contour of the articulating surface in the area substantially coinciding with the damage; and designing the positioning mark to point out the same direction, or joint axis, as at least one of a mark to be made on the side of a recess made in the articulating surface of the joint and a positioning mark on a guide tool to be used for facilitating placement of said implant.

In embodiments, the present invention relates to a design method for designing a guide tool 12 comprising a guide channel 54 for use during cartilage repair in a joint where the design method comprises the placement of a positioning mark 500 on the guide tool, wherein the positioning mark 500 is designed to be aligned with the center 503 of said guide channel in a determined joint axis 501 direction and thereby indicating a placement direction of the guide tool 12 in relation to the selected joint axis 501 during use of the guide tool 12

In another embodiment the present invention relates to a design method for designing a guide tool 12 which is intended for use during cartilage repair in a joint wherein the design method comprises a step for placement of a positioning mark on the guide tool which indicates a placement direction of the guide tool in relation to the joint.

In another embodiment, the present invention relates to a design method for designing a guide tool 12 which is intended for use during cartilage repair in a joint wherein the design method comprises;
  a step for placement or design of a positioning mark on the guide tool wherein the position mark indicates a placement direction of the guide tool in relation to the joint wherein the placement direction is used during placement of the guide tool 12 in the joint.

In different embodiments, the present invention further relates to the different alternatives described below in any combination.

In embodiments, the technology disclosed relates to a design method for designing a guide tool 12 wherein the step for placement of the positioning mark of the guide tool in comparison to the joint where the guide tool is to be placed an in relation to a guide channel comprised in the positioning body 11 of the guide tool 12, and wherein the position mark placed on a top surface 52 indicate to the surgeon of how to place the guide tool on the joint during cartilage repair by that the placement of the positioning mark indicates a placement direction of the guide tool in relation to the joint.

In embodiments, the technology disclosed relates to a design method for designing a guide tool 12 wherein the placement of said positioning mark is on a top surface 52 or top of the guide channel or a surface which is visible for the surgeon during usage.

In embodiments, the technology disclosed relates to a method of designing a guide tool 12 according to the invention further comprising the steps of:
  generating information of a cartilage damage
  using information about said cartilage damage to determine size and shape of implant and/or size and shape of cartilage and/or bone needed to be removed in order to repair said damage
  using information about said cartilage damage to determine size and shape of a cartilage size and spread of a contact surface 52 of the guide tool 12 designed to follow the shape and curvature of the individual cartilage in said joint
  designing a guide tool 12 based on information of cartilage damage and the determined size and shape of implant and/or size and shape of cartilage and/or bone needed to be removed in order to repair said damage.

In embodiments, the technology disclosed relates to a method of designing a guide tool 12 wherein the direction pointed out by the position mark in relation to the joint where the guide is a direction such as; anterior or posterior, right lateral or left lateral, dorsal or ventral, proximal or distal in relation to the placement of the guide tool 12 in a joint.

In embodiments, the technology disclosed relates to a method of designing insert tools designed to comprise positioning marks which is designed to be aligned with the positioning mark of the guide tool 12 when the insert tools are placed in the guide tool in start position, indicating the correct rotational start position of the insert tools to the surgeon during use of the guide tool and insert tools during surgery.

In embodiments, the technology disclosed relate to guide tool or insert tools or an implant designed according to any of the preceding embodiments.

In embodiments, the design method of the technology disclosed may comprises the basic blocks of:
  I. Determining physical parameters for a cartilage damage in a joint and then using this information in order to;
  II. Generate design parameters of a medical implant 10.
  III. Generate design parameters of a guide tool 12 for use during implantation of said implant.

In embodiments, the physical parameters as well as the design parameters are represented as digital data that is processed or generated by specifically designed computer program code portions executed in a data processing system. The system may be fully automated or may comprise portions of computer supported manual steps of for example selections. The design parameters resulting from the process may be stored in a format suitable for use as input in an automated manufacturing process.

In embodiments, the design method includes the further step of:
  IV. Determine a positioning mark placement which placement helps the surgeon to determine the orientation of the placement of the guide tool in a joint, wherein the positioning mark for example may be chosen to be placed in a position on the guide tool which indicate an orientation selected from a position or direction on the patient which is known for the surgeon and based on the anatomy of a patient selected, for example selected from anterior or posterior, right lateral or left lateral, dorsal or ventral, proximal or distal orientation or axis direction, and wherein blocks II-IV of the described design method above can be performed in any desired order.

The technology disclosed relates to a method for designing an implant comprising the steps of designing a contour curvature of the implant so that an articulating surface of the implant is designed to correspond to a simulated healthy articulating surface of a damaged articulating surface of a joint, where the designing of the implant comprises the step of placing, in a virtual 3D view, at least two substantially circular shapes such that each of said circular shapes is partly overlapping at least one other circular shape in that the combined area of the circular shapes is designed to cover, or partly cover, an damaged area, and the step of providing at least one positioning mark on at least one of said at least two substantially circular shapes such that said at least one positioning mark is designed to be used for determining the orientation in which the implant is to be placed in a recess made in a damaged articulating surface of a joint.

In embodiments, the technology disclosed relates to a method for designing an implant comprising the steps of:

designing a contour curvature of the implant so that an articulating surface of the implant is designed to correspond to a simulated healthy articulating surface of a damaged articulating surface of a joint, said designing of the implant comprising placing, in a virtual 3D view, at least two substantially circular shapes such that each of said circular shapes is partly overlapping at least one other circular shape in that the combined area of the circular shapes is designed to cover, or partly cover, a damaged area;

providing at least one positioning mark on at least one of said at least two substantially circular shapes such that said at least one positioning mark is designed to be used for determining the orientation in which the implant is to be placed in a recess made in a damaged articulating surface of a joint; and providing the at least one positioning mark on only one of said at least two substantially circular shapes of the implant so that said at least one positioning mark is designed to be pointing in an anatomic dependent direction, thereby providing for a correct orientation of the implant when inserted in a recess made in a damaged articulating surface of a joint.

In embodiments, the technology disclosed relates to a method for designing an implant comprising the steps of:

designing a contour curvature of the implant so that an articulating surface of the implant is designed to correspond to a simulated healthy articulating surface of a damaged articulating surface of a joint, said designing of the implant comprising placing, in a virtual 3D view, at least two substantially circular shapes such that each of said circular shapes is partly overlapping at least one other circular shape in that the combined area of the circular shapes is designed to cover a damaged area on the articulating surface of a joint;

providing at least one positioning mark on at least one of said at least two substantially circular shapes such that said at least one positioning mark is designed to be used for determining the orientation in which the implant is to be placed in a recess made in a damaged articulating surface of a joint; and designing the at least one positioning mark on at least one of said at least two substantially circular shapes of the implant so that the direction of the positioning of the mark on the contour curvature of the implant, corresponding to a simulated healthy articulating surface reconstructed from a 3D model based on one or more images taken with MRI or CT-scanning of a damaged articulating surface of a joint, is determining the orientation in which the implant is to be placed in the recess.

In embodiments, the technology disclosed relates to a method for designing an implant comprising the steps of:

designing a contour curvature of the implant so that an articulating surface of the implant is designed to correspond to a simulated healthy articulating surface of a damaged articulating surface of a joint, said designing of the implant comprising placing, in a virtual 3D view, at least two substantially circular shapes such that each of said circular shapes is partly overlapping at least one other circular shape in that the combined area of the circular shapes is designed to cover, or partly cover, an damaged area on the articulating surface;

providing at least one positioning mark on at least one of said at least two substantially circular shapes such that said at least one positioning mark is designed to be used for determining the orientation in which the implant is to be placed in a recess made in a damaged articulating surface of a joint; and designing the at least one positioning mark of the implant so that the direction of the positioning mark on the contour curvature of the implant is determining the placement orientation of the implant in a recess in that said placement orientation of said at least one positioning mark is also to be indicated by a mark made on the side of a recess made in the articulating surface of a joint.

In embodiments, the technology disclosed relates to a method for designing an implant comprising the steps of:

designing a contour curvature of the implant so that an articulating surface of the implant is designed to correspond to a simulated healthy articulating surface of a damaged articulating surface of a joint, said designing of the implant comprising placing, in a virtual 3D view, at least two substantially circular shapes such that each of said circular shapes is partly overlapping at least one other circular shape in that the combined area of the circular shapes is designed to cover, or partly cover, an articulate damage;

providing at least one positioning mark on at least one of said at least two substantially circular shapes such that said at least one positioning mark is designed to be used for determining the orientation in which the implant is to be placed in a recess made in a damaged articulating surface of a joint;

designing the shape and size of the implant dependent on the size and shape of the articulate damage and further dependent on the curvature of the contour of the articulating surface in the area substantially coinciding with the articulate damage; and designing the positioning mark to point out a direction in relation to an anatomic dependent direction.

In embodiments, the technology disclosed describes a design method for designing an implant, comprising:

placing, in a virtual 3D view, at least two substantially circular shapes such that each of the circular shapes is partly overlapping at least one other circular shape in that the combined area of the circular shapes is designed to cover, or partly cover, an articulate damage, and providing at least one positioning mark on at least one of the at least two substantially circular shapes such that the at least one positioning mark is designed to be used for determining the orientation in which the implant is to be placed in a recess made in a damaged articulating surface of a joint.

In embodiments, the above-mentioned design methods for designing an implant may further comprise designing a contour curvature of the implant so that an articulating surface 15 of the implant is designed to correspond to a simulated healthy articulating surface of a damaged articulating surface of a joint.

In embodiments, the above-mentioned design methods for designing an implant may further comprise designing the at least one positioning mark of the implant so that the direction of the positioning mark on the contour curvature of the implant is determining the placement orientation of the implant in a recess in that the placement orientation of the at least one positioning mark is also to be indicated by a mark made on the side of a recess made in the articulating surface of a joint.

In embodiments, the above-mentioned design methods for designing an implant may also comprise providing the at least one positioning mark on only one of the at least two substantially circular shapes of the implant so that the at least one positioning mark is designed to be pointing in an anatomic dependent direction, thereby providing for a correct orientation of the implant when inserted in a recess made in a damaged articulating surface of a joint.

In embodiments, the technology disclosed further comprise an implant designed using the above design method for designing an implant, including placing, in a virtual 3D view, at least two substantially circular shapes, and providing at least one positioning mark on at least one of the at least two substantially circular shapes such that the at least one positioning mark is designed to be used for determining the orientation in which the implant is to be placed in a recess made in a damaged articulating surface of a joint.

In embodiments, the technology disclosed describes a medical implant comprising at least one positioning mark is parted from the center of the articulating surface of at least one of said at least two substantially circular shapes of the implant, thereby being adapted to be used for positioning the medical implant in a recess.

In embodiments, the technology disclosed describes a medical implant comprising at least two substantially circular shapes such that each of the circular shapes is partly overlapping at least one other circular shape, and wherein at least one of the at least substantially circular shapes is provided with at least one positioning mark on its surface so that the at least one positioning mark is parted from the center, thereby being adapted to be used for (rotationally) positioning the medical implant.

In embodiments, at least one positioning mark is provided on the articulating surface 15, i.e. the top surface 15 facing the articulating part of the joint, of at least one of the at least two substantially circular shapes of the medical implant.

In certain embodiments, only one of the at least two substantially circular shapes is provided with a positioning mark on its articulating surface 15, i.e. the top surface 15 facing the articulating part of the joint, and the other circular shape(s) is not provided with a positioning mark. The surgeon, or vision system associated with a robot or used in computer-assisted surgery, may then easily detect which of the at least two circular shapes is provided with a positioning mark and then rotationally positioning the medical implant by directing the positioning mark on the articulating surface 15 of one of the circular shapes towards a feature or mark made on e.g. the cartilage surface of a patient or a storage unit for the implant.

In embodiments, at least one positioning mark is provided on the cartilage contacting surface 19, i.e. the side edge surface 19, of at least one of the at least two substantially circular shapes.

In certain embodiments, only one of the at least two circular shapes is provided with a positioning mark on its the cartilage contacting surface 19, i.e. side edge surface, and the other circular shape(s) is not provided with a positioning mark. The surgeon, or vision system associated with a robot or used in computer-assisted surgery, may then easily detect which of the at least two circular shapes is provided with a positioning mark and then rotationally positioning the medical implant by directing the positioning mark on the cartilage contacting surface 19 of one of the circular shapes towards a feature or mark made on e.g. the cartilage surface of a patient or a storage unit for the implant.

The technology disclosed describes a medical implant comprising at least two substantially circular shapes such that each of the circular shapes is partly overlapping at least one other circular shape, and wherein at least one of the at least substantially circular shapes is provided with at least one positioning mark on its surface.

In embodiments, the at least one positioning mark is parted from the center of the articulating surface of at least one of the at least two substantially circular shapes of the implant, thereby being adapted to be used for (rotationally) positioning the medical implant.

In embodiments, only one of the at least two circular shapes is provided with a positioning mark and the other circular shape(s) is not provided with a positioning mark, thereby facilitating the identification of the positioning mark when (rotationally) positioning the implant.

In embodiments, the positioning mark is provided on the articulating surface of at least one of the at least two substantially circular shapes.

In embodiments, only one of the at least two circular shapes is provided with at least one positioning mark on its articulating surface and the other circular shape(s) is not provided with a positioning mark on its articulating surface, thereby facilitating the identification of the positioning mark when positioning the implant.

In embodiments, the positioning mark is provided on the cartilage contacting surface of at least one of the at least two substantially circular shapes.

In embodiments, only one of the at least two circular shapes is provided with at least one positioning mark on its cartilage contacting surface and the other circular shape(s) is not provided with a positioning mark, thereby facilitating the identification of the positioning mark when positioning the implant.

In embodiments, the technology disclosed describes a method for inserting an implant in a joint, comprising:
  providing an implant having at least one positioning mark, wherein the at least one positioning mark is positionally adapted on the surface of the implant to be visible for detection by a vision system, and
  detecting, by the vision system, the at least one positioning mark in relation to at least one of at least one mark made on the side of a recess made in the articulating surface of the joint and at least one pre-determined anatomic dependent direction.

In embodiments, the method for inserting an implant in a joint may further comprise inserting the implant in the recess by directing the at least one implant positioning mark in a direction dependent on the direction of at least one of at least one mark made on the side of a recess made in the articulating surface of the joint and at least one pre-determined anatomic dependent direction, wherein the step of inserting is aided by the step of detecting by the vision system in the above method for inserting an implant in a joint.

In embodiments, the method for inserting an implant in a joint may further comprise detecting an implant positioning mark on the articulating surface 15, i.e. of one substantially circular shape among at least two partly overlapping substantially circular shapes of the implant and/or detecting an implant positioning mark on the cartilage contacting surface 19, i.e. the side edge surface 19, of the implant.

The technology disclosed relates to a method for inserting an implant in a joint, comprising:
  providing an implant having at least one positioning mark, wherein said at least one positioning mark is positionally adapted on the surface of the implant to be visible for detection by a vision system;
  detecting, by the vision system, said at least one positioning mark in relation to at least one of at least one mark made on the side of a recess made in the articulating surface of the joint and at least one pre-determined anatomic dependent direction; and inserting the implant in the recess by directing the at least one implant positioning mark in a direction dependent on the direction of at least one of at least one mark made on the side of a recess made in the articulating surface of the joint and at least one pre-determined anatomic dependent direction, wherein said inserting is aided by said detecting by the vision system.

In embodiments, the technology disclosed relates to a method for inserting an implant in a joint, comprising:

providing an implant having at least one positioning mark, wherein said at least one positioning mark is positionally adapted on the surface of the implant to be visible for detection by a vision system;

detecting, by the vision system, said at least one positioning mark in relation to at least one of at least one mark made on the side of a recess made in the articulating surface of the joint and at least one pre-determined anatomic dependent direction; and inserting the implant in the recess by directing the at least one implant positioning mark in a direction dependent on the direction of at least one of at least one mark made on the side of a recess made in the articulating surface of the joint and at least one pre-determined anatomic dependent direction, wherein said inserting is aided by said detecting by the vision system, and wherein said detecting by said vision system comprises detecting an implant positioning mark on the cartilage contacting surface of the implant.

In embodiments, the technology disclosed relates to a method for inserting an implant in a joint, comprising:

providing an implant having at least one positioning mark, wherein said at least one positioning mark is positionally adapted on the surface of the implant to be visible for detection by a vision system;

detecting, by the vision system, said at least one positioning mark in relation to at least one of at least one mark made on the side of a recess made in the articulating surface of the joint and at least one pre-determined anatomic dependent direction; and inserting the implant in the recess by directing the at least one implant positioning mark in a direction dependent on the direction of at least one of at least one mark made on the side of a recess made in the articulating surface of the joint and at least one pre-determined anatomic dependent direction, wherein said inserting is aided by said detecting by the vision system, wherein said inserting of the implant in the recess is performed by use of at least one mechanical arm, e.g. a robot arm, such that the software-controlled movement of said at least one mechanical arm is aided by said detecting of said at least one implant positioning mark in relation to at least one of at least one mark made on side of the recess and at least one pre-determined anatomic dependent direction.

In embodiments, the technology disclosed relates to a method for inserting an implant in a joint, comprising:

providing an implant having at least one positioning mark, wherein said at least one positioning mark is positionally adapted on the surface of the implant to be visible for detection by a vision system;

detecting, by the vision system, said at least one positioning mark in relation to at least one of at least one mark made on the side of a recess made in the articulating surface of the joint and at least one pre-determined anatomic dependent direction; and inserting the implant in the recess by directing the at least one implant positioning mark in a direction dependent on the direction of at least one of at least one mark made on the side of a recess made in the articulating surface of the joint and at least one pre-determined anatomic dependent direction, wherein said inserting is aided by said detecting by the vision system, wherein said inserting of the implant in the recess is performed by use of at least one mechanical arm, e.g. a robot arm, such that said step of inserting by said at least one mechanical arm is aided by said detecting in that at least one sensor and/or camera is producing at least one of sensor data, at least one still image and video images indicating the relative positioning of at least one of said at least one implant positioning mark in relation to at least one of at least one mark made on side of the recess and at least one pre-determined anatomic dependent direction.

In embodiments, the technology disclosed relates to a method for inserting an implant in a joint, comprising:

providing an implant having at least one positioning mark, wherein said at least one positioning mark is positionally adapted on the surface of the implant to be visible for detection by a vision system;

detecting, by the vision system, said at least one positioning mark in relation to at least one of at least one mark made on the side of a recess made in the articulating surface of the joint and at least one pre-determined anatomic dependent direction; and inserting the implant in the recess by directing the at least one implant positioning mark in a direction dependent on the direction of at least one of at least one mark made on the side of a recess made in the articulating surface of the joint and at least one pre-determined anatomic dependent direction, wherein said inserting is aided by said detecting by the vision system, wherein the contour curvature of said implant corresponds to a simulated healthy articulating surface reconstructed from a 3D model based on one or more images of the joint where the implant is to be inserted.

In embodiments, the method for inserting an implant in a joint may further comprise inserting the implant in the recess by use of at least one mechanical arm, e.g. a robot arm, such that the software-controlled movement of the at least one mechanical arm is aided by the detecting of the at least one implant positioning mark in relation to at least one of at least one mark made on side of the recess and at least one pre-determined anatomic dependent direction.

In embodiments, the technology disclosed describes a method for inserting an implant in a joint using a storage unit, comprising:

providing an implant having at least one positioning mark, wherein the at least one positioning mark is located on the surface of the implant to be visible for detection, and providing a storage unit, e.g. a box, for storing an implant prior to inserting the implant in a recess of a human joint.

In embodiments, the method for inserting an implant in a joint using a storage unit may further comprise a storage unit comprising at least one of a mechanical recess structure and/or holding means adapted for positioning the implant in a rotationally fixed position in the storage unit, where the storage unit further comprises at least one reference feature such as a positioning mark, an edge and/or a corner.

In embodiments, the method for inserting an implant in a joint using a storage unit may further comprise detecting the at least one positioning mark in relation to the at least one reference feature and placing the implant in the storage unit by directing the at least one implant positioning mark on the surface of the implant in a specific, e.g. pre-determined, rotational direction in relation to the at least one reference feature of the storage unit.

In embodiments, the method for inserting an implant in a joint using a storage unit may further comprise the actions of gripping the implant in the storage unit, where the implant is rotationally oriented in accordance with the specific rotational direction of the at least one implant positioning mark in relation to the at least one reference feature of the storage unit, and removing the implant from the storage unit, where the implant is rotationally oriented in accordance with the specific rotational direction of the at least one implant positioning mark in relation to the at least one reference feature of the storage unit when removed from the storage; unit.

In embodiments, the method for inserting an implant in a joint using a storage unit may further comprise the action of inserting the implant in a recess made in a human joint in a correct placement orientation, where the correct placement orientation is determined by how the implant is rotationally positioned in the storage unit in relation to the at least one reference feature of the storage unit.

In embodiments, the technology disclosed describes a storage unit for storing, or holding, an implant prior to inserting the implant in a recess made in a joint, where the storage unit comprises at least one of a mechanical recess structure and/or holding means adapted for positioning the implant in a rotationally fixed position in the storage unit, and where the storage unit further comprises at least one reference feature such as a positioning mark, an edge and/or a corner.

In embodiments, the reference feature of the above storage unit is adapted to be used for rotationally positioning the implant in the storage unit in that at least one positioning mark of the implant may be used for rotationally positioning the implant in relation to the at least one reference feature. The implant may then be placed in the storage unit by directing the at least one implant positioning mark on the surface of the implant in a specific, e.g. pre-determined, rotational direction in relation to the at least one reference feature of the storage unit.

In embodiments, the technology disclosed describes a method for inserting an implant in a joint, comprising:
  providing an implant having at least one positioning mark, wherein said at least one positioning mark is located on the surface of the implant to be visible for detection;
  providing a storage unit, e.g. a box, for storing an implant prior to inserting the implant in a recess of a human joint, wherein said storage unit comprises at least one of a mechanical recess structure and/or holding means adapted for positioning the implant in a rotationally fixed position in the storage unit, and wherein said storage unit further comprises at least one reference feature;
  detecting said at least one positioning mark in relation to said at least one reference feature;
  placing the implant in the storage unit by directing the at least one implant positioning mark on the surface of the implant in a specific, e.g. pre-determined, rotational direction in relation to said at least one reference feature of the storage unit;
  gripping the implant in the storage unit, wherein the implant is rotationally oriented in accordance with said specific rotational direction of the at least one implant positioning mark in relation to said at least one reference feature of the storage unit;
  removing the implant from the storage unit, wherein the implant is rotationally oriented in accordance with said specific rotational direction of the at least one implant positioning mark in relation to said at least one reference feature of the storage unit when removed from the storage unit; and
  inserting the implant in a recess made in a human joint in a correct placement orientation, wherein said correct placement orientation is determined by how the implant is rotationally positioned in said storage unit in relation to said at least one reference feature of the storage unit.

In embodiments, the technology disclosed describes a method for inserting an implant in a joint, comprising:
  providing an implant having at least one positioning mark, wherein said at least one positioning mark is located on the surface of the implant to be visible for detection;
  providing a storage unit, e.g. a box, for storing an implant prior to inserting the implant in a recess of a human joint, wherein said storage unit comprises at least one of a mechanical recess structure and/or holding means adapted for positioning the implant in a rotationally fixed position in the storage unit, and wherein said storage unit further comprises at least one reference feature;
  detecting said at least one positioning mark in relation to said at least one reference feature;
  placing the implant in the storage unit by directing the at least one implant positioning mark on the surface of the implant in a specific, e.g. pre-determined, rotational direction in relation to said at least one reference feature of the storage unit;
  gripping the implant in the storage unit, wherein the implant is rotationally oriented in accordance with said specific rotational direction of the at least one implant positioning mark in relation to said at least one reference feature of the storage unit;
  removing the implant from the storage unit, wherein the implant is rotationally oriented in accordance with said specific rotational direction of the at least one implant positioning mark in relation to said at least one reference feature of the storage unit when removed from the storage unit; and
  inserting the implant in a recess made in a human joint in a correct placement orientation, wherein said correct placement orientation is determined by how the implant is rotationally positioned in said storage unit in relation to said at least one reference feature of the storage unit, wherein said step of detecting said at least one positioning mark in relation to said at least one reference feature when placing the implant in the storage unit is performed by a vision and/or sensor system comprising at least one camera and/or sensor, the vision and/or sensor system is thereby aiding the correct placement of the implant in the storage unit.

In embodiments, the technology disclosed describes a method for inserting an implant in a joint, comprising:
  providing an implant having at least one positioning mark, wherein said at least one positioning mark is located on the surface of the implant to be visible for detection;
  providing a storage unit, e.g. a box, for storing an implant prior to inserting the implant in a recess of a human joint, wherein said storage unit comprises at least one of a mechanical recess structure and/or holding means adapted for positioning the implant in a rotationally fixed position in the storage unit, and wherein said storage unit further comprises at least one reference feature;

detecting said at least one positioning mark in relation to said at least one reference feature;

placing the implant in the storage unit by directing the at least one implant positioning mark on the surface of the implant in a specific, e.g. pre-determined, rotational direction in relation to said at least one reference feature of the storage unit;

gripping the implant in the storage unit, wherein the implant is rotationally oriented in accordance with said specific rotational direction of the at least one implant positioning mark in relation to said at least one reference feature of the storage unit;

removing the implant from the storage unit, wherein the implant is rotationally oriented in accordance with said specific rotational direction of the at least one implant positioning mark in relation to said at least one reference feature of the storage unit when removed from the storage unit; and inserting the implant in a recess made in a human joint in a correct placement orientation, wherein said correct placement orientation is determined by how the implant is rotationally positioned in said storage unit in relation to said at least one reference feature of the storage unit, wherein said steps of gripping the implant in the storage unit, removing the implant from the storage unit and inserting the implant in the human joint in a correct placement orientation are performed by the use of at least one mechanical arm, e.g. a robot arm, and wherein said step of inserting said implant in the correct placement orientation in the recess of the joint is determined by how the implant is rotationally positioned/oriented in said storage unit in that the software-controlled movement of the mechanical arm from the storage unit to the recess is pre-programmed based on the rotational positioning/orientation of the implant in the storage unit.

BRIEF DESCRIPTION OF THE FIGURES

The invention will be further explained with reference to the accompanying drawings which are exemplified embodiments according to the invention and not limiting the scope of the invention:

FIGS. 15a-b show a medical implant according to the invention which comprises two substantially circular shapes, e.g. designed from using a virtual model comprising two substantially circular shapes, where one of the circular shapes is provided with a positioning mark on its cartilage contacting surface 19, i.e. side edge surface 19.

DETAILED DESCRIPTION OF THE INVENTION

Design Method

The present invention is directed to a system, comprising a method, apparatus and computer programs, for designing a guide tool 12 comprising a positioning mark 500, and/or medical implant comprising a positioning mark 500, and/or associated tools comprising positioning marks and wherein said guide tool 12 insert tool 502 and implant 10 all comprises a positioning mark 500 marking out the same direction or axis in relation to the joint during use when replacing damaged cartilage in a joint. The associated set of tools is devised for the placement of an implant that replaces damaged cartilage in a joint and is adapted to the specific implant as well as a specific joint for which the implant is intended. The surgical kit provided by the present invention has the effect that successful implant insertion is less dependent on surgical circumstances and the skills of the surgeon compared to previously known implants. Due to the design and the function of using the positioning marking in guide tool and/or implant and/or inert tools gives improved implantation precision and a precise desired placement of the implant in the joint every time. The precision of the surgery is "built in" into the design of the tools.

Figure 1:
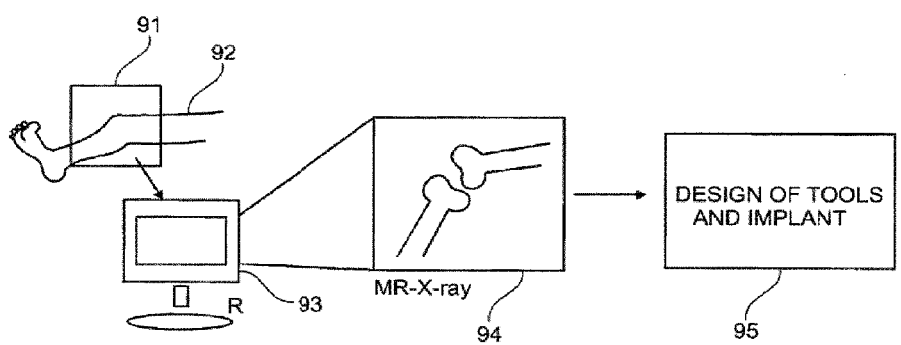
FIG. 1 schematically illustrates parts of the design process according to an embodiment of the inventive concept for designing a surgical kit.

FIG. 1 shows an example of a surgical kit designed according to a method of one embodiment of the present invention. This particular exemplifying embodiment of a surgical kit according to the invention is especially adapted for cartilage replacement at the femur of a knee joint. The invention may however be applied for cartilage replacement in an articulating surface in any other joint in the body, e.g. elbow, ankle, finger, hip, toe and shoulder. The guide tool 12 according to the invention may be equipped with a guide-channel 13 and a positioning body 11 and may be used together with an implant 10, and a drill guide 8, a cutting tool 6, which in this exemplifying embodiment is a punch, a drill-bit 8, preferably equipped with a depth gauge 1 and/or a reamer-bit 4, preferably equipped with a depth gauge 3, and/or a hammer tool 35 and/or a reamer guide 28, and/or implant dummy 36. The details of examples of insert tools 502 which may be used inside the guide tool 12 are further described and exemplified below.

FIG. 1 schematically illustrates the design process according to an embodiment of the inventive concept for designing a guide tool and/or insert tools 502 and/or implant 10.

The design system comprises the basic blocks of:

I. Determining physical parameters for a cartilage damage in a joint and then using this information in order to;

II. Generate design parameters of a medical implant 10.

III. Generate design parameters of a guide tool 12 for use during implantation of said implant.

The physical parameters as well as the design parameters are represented as digital data that is processed or generated by specifically designed computer program code portions executed in a data processing system. The system may be fully automated or may comprise portions of computer supported manual steps of for example selections. The design parameters resulting from the process are stored in a format suitable for use as input in an automated manufacturing process.

IV. Determine a positioning mark placement which placement helps the surgeon to determine the orientation of the placement of the guide tool in a joint and wherein the positioning mark 500 for example may be chosen to be placed in a position on the guide tool which indicate an orientation selected from a position or direction on the patient which is known for the surgeon and based on the anatomy of a patient selected, for example selected from anterior or posterior, right lateral or left lateral, dorsal or ventral, proximal or distal orientation or axis direction.

and wherein blocks II-IV above can be performed in any order.

In one embodiment according to the invention the design system is a system to design a guide tool 12 to be used to guide inserts tools and/or an implant or other cartilage repair objects comprises the basic blocks of:

I. Determining physical parameters for a cartilage damage in a joint and then using this information in order to;

II. Generate design parameters of a medical implant 10.

III. Generate design parameters of a guide tool 12 for use during implantation of said implant. The physical parameters as well as the design parameters are represented as digital data that is processed or generated by specifically designed computer program code portions executed in a data processing system. The system may be fully automated or may comprise portions of computer supported manual steps of for example selections. The design parameters resulting from the process are stored in a format suitable for use as input in an automated manufacturing process.

IV. Determine placement for placement of a positioning mark 500 on the guide tool wherein the positioning mark 500 is designed to be aligned with the center 503 of said guide channel 54 in a determined joint axis 501 direction and thereby indicating a placement direction of the guide tool 12 in relation to the selected joint axis 501 during use of the guide tool 12. The direction is also indicated by placement of the positioning mark 500 of the guide tool 12 on a side of the guide channel which faces the chosen direction in relation to the joint.

The placement of the positioning mark on a guide tool, may be on top of the guide channel 54 or on top of the positioning body 11 on the side of the guide channel or at any place visible for the surgeon using the guide tool.

and wherein blocks II-IV above can be performed in any order.

In one embodiment according to the invention, the insert tools 502 and or the implant 10 is also designed to comprise a position mark 500, and the position of the position mark is designed to be on a surface which is visible for the surgeon during surgery and use of the insert tools 502 and or implant 10. Example of such surfaces are on the top of the insert tools, on a surface facing the surgeon during use of the insert tools, for example on a surface opposite to the surface facing the cartilage damage. The positioning marking 500 of an implant 10 may for example be on the articulating surface 15 of the implant, preferably not placed in the center but parted from the center of the implant or on a surface which is visible for the surgeon, or for example on a top surface of an insert tool pointing in the opposite direction compared to the cartilage contact surface 50 of the positioning body 11.

According to certain aspects, the technology disclosed provides a design method that allows for producing an implant which is easy to fit to an individual damage and an individual patient. The design build-up method comprises choosing size, at least two circular shapes, implant thickness, implant surface shape, articular surface etc. for each implant. This build-up makes the proposed solution and implant unique and easy to individualize, but still suitable for large scale industrial manufacturing. The design process further comprises designing the implant to have at least one positioning mark on the surface of one of the circular shapes, where the positioning mark is adapted to be used for pointing out a direction for placement of the implant in a recess. The circular shapes building up the implant makes the implant easy to place by drilling and/or reaming, thereby providing for a fit of each implant in every patient.

According to certain aspects of the technology disclosed, the positioning or location of the at least one positioning mark on the surface of the implant may be determined based on one or more of images taken of the damaged cartilage surface of a joint. A technical effect of introducing at least one positioning mark on the implant is that the contour curvature of an articulating surface 15 of the implant body, which is built up from the at least two circular shapes, may be to enable or facilitate orientating and positioning of the implant (e.g. by the surgeon or a robot) so that the implant is aligned to the cartilage surface surrounding the recess in a correct way. Furthermore, by introducing at least one positioning mark on the implant, the contour curvature of an articulating surface 15 of the implant body may be (rotationally) oriented/positioned in a recess to correspond to a simulated healthy cartilage reconstructed from one or more of the images taken of the damaged cartilage surface of the joint.

Embodiments herein relate to design methods for design of an implant having at least one positioning mark where the design of the implant is based on a 3D virtual model of an implant. The design method may then comprises identifying a damage area, presenting a virtual 3D view of the identified damage area and creating a 3D virtual implant comprising virtually placing in the 3D view a shape. The area of the shape then covers or partly covers the identified damage area, producing an implant based on the created 3D virtual implant. The shape comprises at least two substantially circular shapes, where the surface of at least one of the at least two substantially circular shape is designed to be provided with at least one positioning mark. Each circular shape may partly overlap at least one other circular shape, and the area of the circular shapes may cover or partly cover the identified damage area.

The method for designing the implant by building up the implant from at least two circular shapes may further comprise placing at least two points, each from where an axis will origin from on the bone surface of the joint in or nearby the damage area or on a simulated bone surface which is a virtually created surface covering the damage area. In embodiments, each circular shape may comprise a respective axis, and the overlap of the circular shapes may depend on the selection of diameter for the respective circular shape in combination with the selection of distance between an axis of one circular shape and another axis of another circular shape.

In certain embodiments, the selections of diameter for respective circular shape and distance between axes may be combined with the selection of a desired coverage for the implant of the damage area. In some embodiments, the identifying of a damage area in a patient may be performed by taking CT, CBCT, MRI images or the like of a joint of a patient and using the images to create a 3D view of the bone and/or cartilage area using for example a software program useful for virtual 3D animation. In embodiments, the design step of using CT, CBCT, MRI images of a joint to create the 3D view may include determining the position or location on the surface of the implant for at least one positioning mark. The position for the at least one positioning mark on the surface may then be determined from the CT, CBCT, MRI images of the joint of a patient, thereby being designed for providing for a correct rotational positioning/orientation of the implant in a recess made in the joint.

In certain embodiments, the positioning mark provided on the surface of at least one of the plurality of circular shapes of the implant is adapted to be used for alignment of the positioning mark of the implant to a certain anatomic dependent direction associated with the joint in which the implant is to be inserted. The introduction of a positioning mark on the surface of one circular shape may be particularly beneficial when a plurality of placement options for inserting the implant in a recess exist, e.g. when the implant to be inserted is built-up with a plurality of substantially circular shapes having essentially the same diameter.

By using the design method according to different embodiments herein, a surgeon, or a robot, is provided with a precise way to correctly place and rotationally position an implant in a recess made in the joint. According to embodiments of the design methods and system of the technology disclosed, implant shapes may be built individually depending on cartilage damage and location of damage in the joint. This provides for a selection from different sizes of circular shapes, or substantially circular shapes, which are partly overlapping each other and which may or may not be individually selected for one patient, allowing for the surgeon to choose an implant which fits the size and shape of the specific bone and or cartilage damage or defect, and further gives the surgeon an easy to use design method and tool set for making the excisions needed.

In a certain embodiment, at least one positioning mark provided on an implant which is designed to be built-up from and comprise one substantially circular shape or a plurality of overlapping substantially circular shapes may provide guidance to a surgeon, or a robot having a vision system. The vision system may then be adapted and configured for detecting the at least one of the positioning mark on the surface of the implant in relation to a mark made on side of a recess, where the mark made on side of the recess may be made in a pre-determined anatomic dependent direction or in a direction/position determined from the process for designing the implant. The direction/position of the positioning mark may then be determined from at least one image taken of the damaged joint. Following detection by the vision system of the at least one of the positioning mark on the implant and the mark made on side of the recess, the implant may be correctly inserted/oriented in the recess by directing the positioning mark, e.g. provided on the surface of one of the implant's circular shapes, in at least one of the direction of a mark previously made on side of the recess (which position may be determined in the design process) and in a pre-determined anatomic dependent direction. Here, by correctly inserted/oriented, it is meant that the contour curvature of an articulating surface 15 of the implant, which may be designed based on a 3D virtual implant created using one or more CT, CBCT, MRI images or the like of a joint of a patient, corresponds to a simulated healthy cartilage reconstructed from one or more of the images taken of the damaged cartilage surface of the joint and that the contour curvature of the articulating surface 15 of the implant may further be aligned to the cartilage surface surrounding the recess.

In a certain embodiment of a surgical method using the technology disclosed, no mark is made on side of the recess but the detection of the positioning mark on the surface of at least one of the circular shapes, which may be detected by e.g. a vision system associated with a robot or in computer-assisted surgery, is used for pointing the positioning mark in a pre-determined anatomic dependent direction so that the implant is correctly placed in the recess. This may provide the same effect as mentioned above in that the implant, which is designed based on a 3D virtual implant created using one or more CT, CBCT, MRI images or the like of a joint of a patient, may be correctly inserted/oriented in the recess in that the contour curvature for the articulating surface 15 of the implant corresponds to a simulated healthy cartilage reconstructed from one or more of the images taken of the damaged cartilage surface of the joint and in that the contour curvature for the articulating surface 15 of the implant may further be aligned to the cartilage surface surrounding the recess.

In certain embodiments, a guide tool may further be used in the surgical method of inserting an implant in the recess and the positioning mark provided on the implant may then be pointing out a direction for placement of the implant in a recess in relation to a joint axis with the guide tool, or an anatomic dependent direction, and may point out the same direction as a positioning mark on the guide tool used for placing the implant.

In embodiments, the contour curvature for an articulating surface 15 of the implant body of the implant is built-up with at least two substantially circular shapes and is dependent on a determined surface curvature of the cartilage and/or the subchondral bone. At least one of the articulating surface 15 and the cartilage contacting surface 19 of at least one of the circular shapes is then provided with a positioning mark which is parted from the center of the implant to thereby be designed to be pointing out a pre-determined anatomic dependent direction and/or which is designed to be pointing in the direction of a mark made on side of the recess, where the mark made on the recess is indicating the direction in which the implant is to be placed. The articulating surface of the implant may then have a curvature that corresponds to a simulated healthy cartilage reconstructed from an image taken e.g. with MRI or CT-scanning of the damaged cartilage surface of the joint.

In certain embodiments, the positioning mark is placed on either the articulating surface 15 or the cartilage contacting surface 19 of one of the plurality of circular shapes of the implant and is adapted to be used for alignment of the positioning mark of the implant, i.e. aligning the implant, to a mark made on side of the recess, where the mark made on the recess is indicating the direction in which the positioning mark on the surface of one of the plurality of circular shapes is to be directed to rotationally position the implant correctly in the recess.

According to certain aspects, the technology disclosed describes a design method for designing of an individually customized implant, where a second virtual model making step comprises making a 3D model of a virtual implant including a step of virtually placing in the 3D view at least two circular shapes, where each of the at least two circular shapes is partly overlapping at least one other circular shape.

According to other aspects, the technology disclosed describes a design method for design of an individually customized implant provided with a positioning mark and comprising at least two substantially circular shapes, where each circular shape comprises an axis and where an overlap of the circular shapes depends on selection of diameter of the substantially circular shapes in combination of selection of closeness of an axis of one circular shape in relation to another axis of another circular shape in combination with selection of desired coverage for the implant of the bone and/or cartilage damage.

In an automated process, a computer program, for example a radiography software program, could be adapted to scan the images for predetermined characteristics of an area and or spread, curvature and or a location of bone and/or cartilage damage in the image data. The automatically marked 2D images may then be combined into a 3D view which may be called the damage representation CAD animation model. The size of the area which is of interest to map or to create a 3D view of is usually not depending of the size of the cartilage damage and the type of joint or bone part which is to be repaired, usually the surgeon does not know where in the joint the damage is located before taking images of the patients joint, therefore typically, images of the whole bone and or cartilage area of the joint are used to create a virtual 3D view. A virtual 3D view is a joint representation CAD animation model which may be selected to show the bone and or cartilage area, the bone and or cartilage damage, placement of virtual implants etc.

In certain embodiments, a first damage identification step of the design method according to embodiments herein comprises identifying a bone and/or cartilage area in a patient by taking images of the injury or damage in the joint of a patient and then use these images of the individual patient's bone and/or cartilage area to create a joint representation CAD animation model. In embodiments, the technology disclosed relates to a method for designing an implant comprising designing the implant so that the contour curvature of an articulating surface 15 of the implant is designed to correspond to a simulated healthy articulating surface of a damaged articulating surface of a joint. The method for designing the implant may then comprise placing, in a virtual 3D view, at least two substantially circular shapes such that each of the circular shapes is partly overlapping at least one other circular shape in that the combined area of the circular shapes is designed to cover, or partly cover, a damaged area. The method for designing the implant by creating a virtual 3D view may further include determining a position for an implant positioning mark and/or the actual design of the positioning mark in the same design process steps that include placing the at least two substantially circular shapes in the virtual 3D view.

Hence, the method for designing the implant may further include designing the implant by providing at least one positioning mark on at least one of the at least two substantially circular shapes in the virtual 3D view such that the at least one positioning mark is designed to be used for determining the rotational orientation in which the implant is to be placed in a recess made in a damaged articulating surface of a joint. In embodiments, the design method may further includes providing the at least one of the at least one positioning mark on the articulating surface 15, i.e. the top articulating surface 15, of one of the at least two substantially circular shapes and/or providing the at least one positioning mark on the cartilage contacting surface 19, i.e. the side edge surface, of one of the at least two substantially circular shapes of the implant. The positioning mark on the articulating surface 15 is then parted from the center of the implant to be adapted for rotationally positioning the implant. In embodiments, the positioning mark on the articulating surface 15 may preferably be placed on the surface peripheral of the articulating surface 15.

The design method may further include designing the contour curvature of the implant so that the articulating surface 15 of the implant and the at least one positioning mark correspond to a simulated healthy articulating surface reconstructed from a 3D model based on one or more images taken with MRI or CT-scanning of a damaged articular surface of a joint. In certain embodiment, the design method may then include designing the implant by providing the at least one positioning mark on only one of the at least two substantially circular shapes in the virtual 3D view for the implant so that the at least one positioning mark is designed to be pointing in an anatomic dependent direction or a mark to be made on side of a recess in which the implant is to be inserted, thereby providing for a correct rotational orientation of the implant when inserted in the recess made in a damaged articulating surface of the joint.

In other embodiments, the design method may include designing the at least one positioning mark of the implant so that the direction of the positioning mark on the contour curvature of the articulating surface 15 of one circular shape of the plurality of circular shapes of the implant is determining the rotational placement orientation of the implant in a recess in that the placement direction of the at least one positioning mark is also to be indicated by a mark made on the side of a recess made in the articulating surface of a joint. The positioning mark on the articulating surface 15 of one circular shape of the plurality of circular shapes is then parted from the center of the implant to be adapted for rotationally positioning the implant. In embodiments, the positioning mark on the articulating surface 15 of one circular shape of the plurality of circular shapes may preferably be placed on the surface peripheral of the articulating surface 15.

In embodiments, the technology disclosed relates to a method for inserting an implant in a joint comprising providing an implant having at least one positioning mark, wherein the at least one positioning mark is positionally adapted on the surface of the implant to be visible for detection by a vision system. The method for inserting an implant may then further include detecting, by the vision system, the at least one positioning mark in relation to at least one of at least one mark made on the side of a recess in the articulating surface of the joint and at least one pre-determined anatomic dependent direction. The insertion of the implant in the recess may be performed by directing the at least one implant positioning mark in a direction dependent on the direction of at least one of at least one mark made on the side of a recess made in the articulating surface of the joint and at least one pre-determined anatomic dependent direction. The insertion may then be aided by the detecting by the vision system.

In embodiments, the inserting of the implant in the recess may be performed by directing the at least one implant positioning mark in the direction of at least one of at least one mark made on the side of the recess on the articulating surface. In embodiments, the method for inserting an implant in a joint may then include detecting, by a vision system, both the mark made on the side of the recess and at least one implant positioning mark on the articulating surface 15, i.e. the top articulating surface 15, of one substantially circular shape among at least two partly overlapping substantially circular shapes of the implant. The positioning mark on the articulating surface 15 of one circular shape of the plurality of circular shapes is then parted from the center of the implant to be adapted for rotationally positioning the implant. In embodiments, the positioning mark on the articulating surface 15 of one circular shape of the plurality of circular shapes may preferably be placed on the surface peripheral of the articulating surface 15. In other embodiments, the method for inserting an implant in a joint may include detecting, by a vision system, both the mark made on the side of the recess and at least one implant positioning mark on the cartilage contacting surface 19, i.e. the side edge surface 19, of the implant.

Robotic surgery, computer-assisted surgery, and robotically-assisted surgery are terms for technological developments that use robotic systems to aid in surgical procedures. Robotically-assisted surgery was developed to overcome the limitations of pre-existing minimally-invasive surgical procedures and to enhance the capabilities of surgeons performing open surgery.

In the case of robotically-assisted minimally-invasive surgery, instead of directly moving the instruments, the surgeon may use one of two methods to control the instruments, either a direct telemanipulator or through computer control. A telemanipulator is a remote manipulator that allows the surgeon to perform the normal movements associated with the surgery whilst the robotic arms carry out those movements using end effectors and manipulators to perform the actual surgery on the patient. In computer-controlled systems, the surgeon uses a computer to control the robotic arms and its end-effectors, though these systems can also still use telemanipulators for their input. One advantage of using the computerised method is that the surgeon does not have to be present, but can be anywhere in the world, leading to the possibility for remote surgery. In the case of enhanced open surgery, autonomous instruments may replace traditional steel tools, performing certain actions with much smoother, feedback-controlled motions than could be achieved by a human hand. The main object of such smart instruments is to reduce or eliminate the tissue trauma traditionally associated with open surgery without requiring more than a few minutes' training on the part of surgeons. This approach seeks to improve open surgeries that have so far not benefited from minimally-invasive techniques.

In embodiments of the technology disclosed, a computer-assisted surgical system may be used for inserting the implant in a recess. Different types of computer-assisted surgical systems can be used for pre-operative planning, surgical navigation and to assist in performing surgical procedures.

Robotically-assisted surgical (RAS) devices are one type of computer-assisted surgical system. Sometimes referred to as robotic surgery, RAS devices enable the surgeon to use computer and software technology to control and move surgical instruments through one or more tiny incisions in the patient's body (minimally invasive) for a variety of surgical procedures. The benefits of a RAS device may include its ability to facilitate minimally invasive surgery and assist with complex tasks in confined areas of the body. The device is not actually a robot because it cannot perform surgery without direct human control.

RAS devices generally have several components, which may include at least one of the following components:
1) a console, where the surgeon sits during surgery. The console is the control center of the device and allows the surgeon to view the surgical field, e.g. through a 3D endoscope, and control movement of the surgical instruments;
2) a bedside cart that may include at least one mechanical arm, at least one camera and surgical instruments that the surgeon may or may not control during surgical procedures; and
3) a separate cart that may contain supporting hardware and software components, such as an electrosurgical unit (ESU), suction/irrigation pumps, and light source for the camera.

Most surgeons use multiple surgical instruments and accessories with the RAS device, such as scalpels, forceps, graspers, dissectors, cautery, scissors, retractors and suction irrigators.

In these days, there are a lot of medical devices in operation room. In addition, several surgical master-slave robots have been commercialized, and are becoming common.

In embodiments of the technology disclosed, a surgical robot comprising control software may be used for inserting the implant in a recess. By introducing surgical robots, it is possible to perform more precise insertion of the implant in the recess. In certain embodiments, the surgeon may uses one of two methods to control the instruments, either a direct telemanipulator or through computer control, and to insert the implant in the recess.

Typically, the control software has hardware dependencies based on actuators, sensors and various kinds of internal devices.

The method for inserting an implant in a recess according to the present invention may include inserting the implant in the recess by use of at least one mechanical arm, e.g. a robot arm, such that the software-controlled movement of the at least one mechanical arm is aided by the detecting of at least one implant positioning mark in relation to at least one of at least one mark made on side of the recess and at least one pre-determined anatomic dependent direction. The method for inserting an implant may then further include detecting, by a vision system, the at least one positioning mark in relation to at least one of at least one mark made on the side of a recess made in the articulating surface of the joint and at least one pre-determined anatomic dependent direction. The insertion of the implant in the recess may be performed by directing the at least one implant positioning mark in a direction dependent on the direction of at least one of at least one mark made on the side of a recess made in the articulating surface of the joint and at least one pre-determined anatomic dependent direction. The insertion is then aided by the detecting by the vision system.

In embodiments, the inserting of the implant in the recess may be performed by directing the at least one implant positioning mark in the direction of at least one of at least one mark made on the side of the recess on the articulating surface. The method for inserting an implant in a joint may then include detecting, by a vision system, an implant positioning mark on the articulating surface 15, i.e. the top surface 15, of one substantially circular shape among at least two partly overlapping substantially circular shapes of the implant. In other embodiments, the method for inserting an implant in a joint may include detecting, by a vision system, an implant positioning mark on the cartilage contacting surface 19, i.e. the side edge surface 19, of the implant. The positioning mark on the articulating surface 15 of at least one circular shape of the plurality of circular shapes is then parted from the center of the implant to be adapted for rotationally positioning the implant. In embodiments, the positioning mark on the articulating surface 15 of at least one circular shape of the plurality of circular shapes may preferably be placed on the surface peripheral of the articulating surface 15.

In certain embodiments, the inserting of the implant in the recess is performed by use of at least one mechanical arm, e.g. a robot arm, such that the inserting of the implant by the at least one mechanical arm is aided by the detecting by the vision/sensor system in that at least one sensor and/or camera is producing at least one of sensor data, still images and video images indicating the relative positioning of at least one of the at least one implant positioning mark in relation to at least one of at least one mark made on side of the recess and at least one pre-determined anatomic dependent direction.

In yet another embodiment, the method for inserting an implant further includes providing a guide tool comprising a positioning feature/mark and making, by one of a surgeon and a mechanical arm such as a robot arm, a mark on the side of a recess made in an articulating surface of the joint in the direction of the positioning mark of the guide tool, thereby determining the future placement orientation of the implant.

In embodiments, the technology disclosed relates to a surgical method and a storage unit for storing the implant prior to inserting the implant in a human joint comprising providing an implant having at least one positioning mark, where the at least one positioning mark may be positioned or located on the surface of the implant to be visible for detection. The method for inserting the implant may further involve a storage unit, e.g. a box, for storing an implant prior to inserting the implant in a recess of a human joint where the storage unit comprises at least one reference feature such as a positioning mark. The storage unit may comprise a mechanical recess structure and/or holding means adapted for fixing or holding the implant in a rotationally fixed position in the storage unit and the at least one reference feature of the storage, e.g. a corner/edge of the storage unit or a positioning mark on the surface of the storage unit, is adapted and/or designed to be used to determine the rotational orientation of the implant when placed in the storage unit.

The method for inserting the implant may further include detecting the at least one positioning mark in relation to the at least one reference feature and placing the implant in the storage unit by directing the at least one implant positioning mark on the surface of the implant in a specific, e.g. pre-determined, rotational direction in relation to the at least one reference feature of the storage unit. The method for inserting the implant in a human joint may further include removing the implant from the storage unit in that the implant is rotationally oriented in accordance with the specific rotational direction of the at least one implant positioning mark in relation to the at least one reference feature of the storage unit. This provides the effect that the implant is removed from the storage unit and inserted in a recess made in a human joint in a correct or more accurate rotational placement orientation. The correct, or more accurate, rotational placement orientation may then be determined by how the implant is rotationally positioned in the storage unit in relation to the at least one reference feature of the storage unit.

In embodiments, the detection of the at least one implant positioning mark in relation to the at least one reference feature when placing the implant in the storage unit is performed by a vision and/or sensor system comprising at least one camera and/or sensor. The vision and/or sensor system may thereby be used for facilitating the correct placement of the implant in the storage unit.

In embodiments, at least one of the steps of gripping the implant in the storage unit, removing the implant from the storage unit and the inserting the implant in the human joint (in a correct placement orientation) may be performed by the use of at least one mechanical arm, e.g. a robot arm. The step of inserting the implant in the correct placement orientation in the recess of the joint may then be determined by how the implant is rotationally positioned/oriented in the storage unit in that the software-controlled movement of the mechanical arm from the storage unit to the recess is pre-programmed based on the rotational positioning/orientation of the implant in the storage unit.

In embodiments, the technology disclosed relates to a storage unit for storing an implant prior to inserting the implant in a human such as a human joint. The storage unit may then be provided with at least one reference feature, such as a positioning mark, which is adapted to be used for providing a correct or more accurate rotational orientation of the implant when placing the implant in the storage unit.

The implant may then be placed in the storage unit by directing at least one implant positioning mark on the surface of the implant in a specific, e.g. pre-determined, rotational direction in relation to at least one reference feature of the storage unit. In certain embodiments, the implant is placed in the storage unit by directing at least one implant positioning mark in the direction of a reference feature, e.g. a corner, edge or holding means of the storage unit, e.g. a box, or a positioning mark provided on the surface of the storage unit.

The storage unit may further be adapted to allow for gripping of the implant in the storage unit so that the implant is rotationally oriented in accordance with a specific rotational direction of the at least one implant positioning mark in relation to the at least one reference feature or holding means of the storage unit. The design and location of the at least one implant positioning mark on the surface of the implant may then be dependent on the design and location of the at least one reference feature of the storage unit.

In embodiments, the storage unit may be configured so that at least one of the steps of gripping the implant in the storage unit, removing the implant from the storage unit and inserting the implant in the human joint may be performed by use of at least one mechanical arm, e.g. a robot arm. The software-controlled movement of the mechanical arm from the storage unit to the recess may then be pre-programmed based on the rotational positioning/orientation of the implant in the storage unit and the rotational placement orientation of the implant in a recess of a human joint may then be determined by how the implant is rotationally positioned in the storage unit in relation to the at least one reference feature of the storage unit.

In another embodiment, the present invention relates to an individually design of surgical kit and/or a guide tool 12 comprising position marks and to a design method for design of such a kit.

In one embodiment, the placement of the position mark is determined by first determine the size, spread and placement of the cartilage contact surface in a computer model and then use this model of a cartilage contact surface and determine a direction, based on the virtual placement of the model cartilage contact surface on the simulated joint (or on an image of an individual 3D image of a joint surface). And after deciding the direction, place a virtual position mark on that place, which may be a place pointing in any direction in comparison to the placement of the guide tool in the joint, for example pointing in an anterior direction etc. The position mark is designed to be placed on a surface of the positioning body of the guide tool 12 which is a surface pointing in an opposite direction compared to the cartilage contact surface of the positioning body. The said placement of the positioning mark 500 is also determined in relation to the design of the guide channel 54 and its placement on the cartilage contact surface 50 of the guide tool 12.

This placement of said position mark on the guide tool 12 may then be used by the surgeon in order to place the individually designed guide tool in the right placement during surgery by knowing in which direction the positioning mark 500 is designed to point.

For example, if a guide tool 12 is designed to point in an anterior direction during knee surgery, and the guide tool 12 then has a positioning mark 500, placed for example on a side or on top of the guide channel or on a top surface 52 of the positioning body 12. Then the surgeon knows that the positioning mark 500 should point in an anterior direction if he placed the guide tool in a correct direction, see for an example in FIG. 2 for a placement of an implant comprising a positioning mark 500 in an anterior direction in relation to the knee joint.

A further effect of the invention is that the size of the cartilage contact surface can be designed to be smaller in area spread because the surgeon now know due to the positioning mark if the guide is placed in the correct position from start and does not need a large cartilage contact surface of the guide tool to "feel" when the guide is placed correctly.

In other embodiment, the design of the insert tools are also designed to comprise a position marking and the position marking of the insert tools is designed to coincide with the positioning mark of the guide tool 12 when the insert tools are placed within the guide tool in their first positions or their starting position. This alignment gives instruction to the surgeon about rotational start direction when using the insert tools 502.

Figure 6:
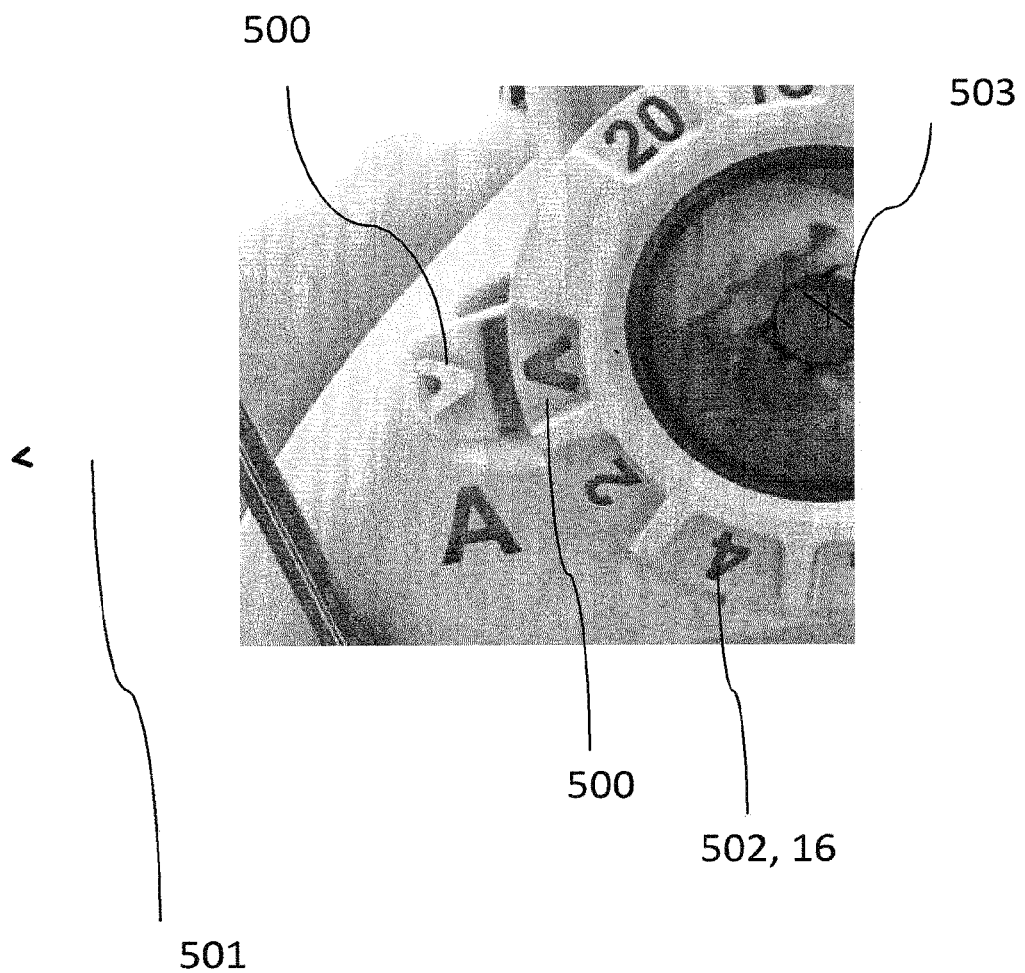
FIG. 6 shows a guide tool according to the invention placed on the cartilage in a joint and further comprising a height adjustment insert tool placed in start position inside the guide channel, and wherein the positioning mark of the guide tool and the positioning mark of the height adjustment insert tool are aligned and wherein it is shown that the center of the guide channel is aligned with the positioning markings 500 in an anterior direction of a knee joint.

This is exemplified in FIG. 6 wherein a height adjustment device is used as an insert tool 502 and in FIG. 6, the insert tool is placed in a starting position where both the positioning mark 500 of the insert tool is aligned with the positioning mark 500 of the guide tool 12.

Figure 2:
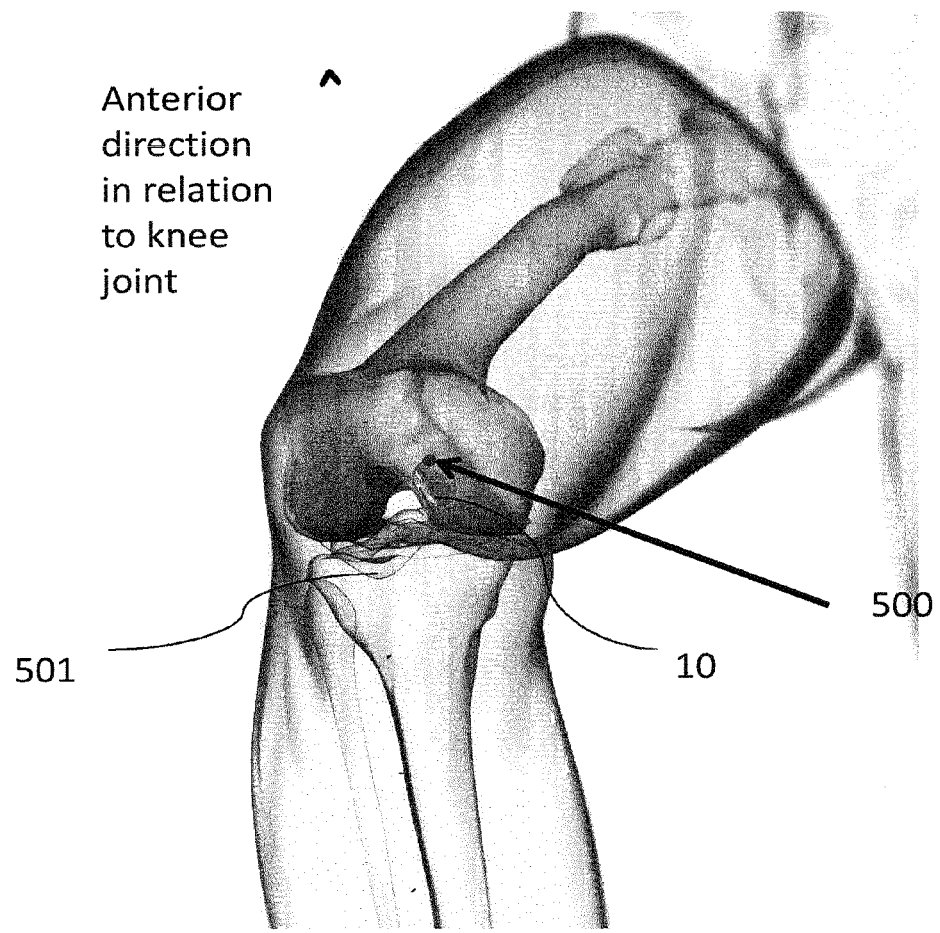
FIG. 2. Shows a medical implant comprising a positioning mark placed using a guide tool according to the invention and wherein the positioning mark is placed in an anterior position in relation to a knee joint.

See for example FIG. 2 for further examples of the invention where the implanted implant has a position mark pointing in an anterior direction compared to the joint and limb. The positioning mark 500 on the guide tool 12 used during placement of this implant also pointed in the same direction, se for example in FIG. 5.

Figure 4A:
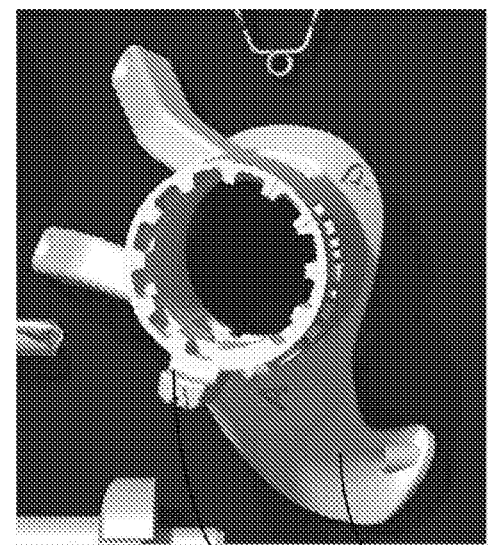
FIG. 4a shows a guide tool comprising a positioning mark placed on top of the guide channel in anterior direction (compared to the relation of placement of the guide tool in the joint and in relation to the guide channel).
Figure 4B:
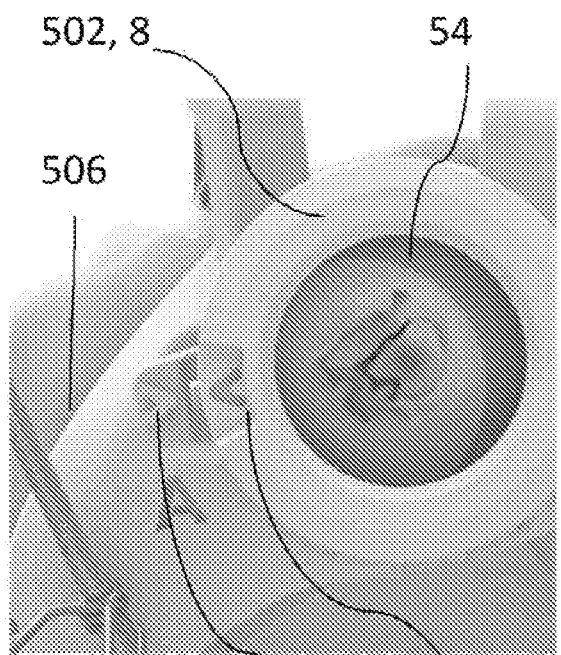
FIG. 4b shows an insert tool, in this example a reamer guide placed inside the guide channel of the guide tool in a start position and where the positioning mark of the guide channel and the positioning mark of the insert tool are aligned.

FIG. 4-10 shows use of the guide tool of the invention together with different insert tools, FIG. 4a shows the guide tool without insert tools. FIG. 4b shows use of a drill guide 8 inside the guide channel 54 of the guide tool 12.

Figure 5:
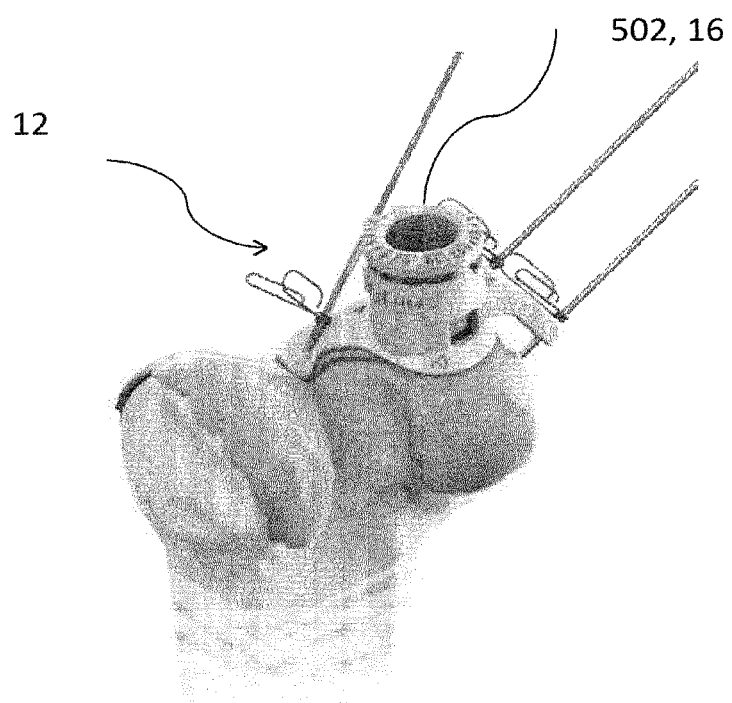
FIG. 5 shows a guide tool according to the invention placed on the cartilage in a joint and further comprising a height adjustment insert tool

FIG. 5 shows the guide tool 12 together with a height adjustment device 16 inside the guide channel. A height adjustment device 16 according to the invention comprises a male part 47 and a female receiving part 48 which when used together allows for stepwise adjustment of drill depth.

In one embodiment the present invention comprises a design method for design of a surgical kit where one part is related to the design of a guide tool according to the present invention described herein and one part is directed to the design of insert tools 502 comprising positioning marks 500 which is aligned with the positioning marks of the designed guide tool when inserted in the guide tool 12 in a start position which indicating the correct rotational start position of the insert tools to the surgeon during use of the guide tool and insert tools during surgery.

Figure 11:
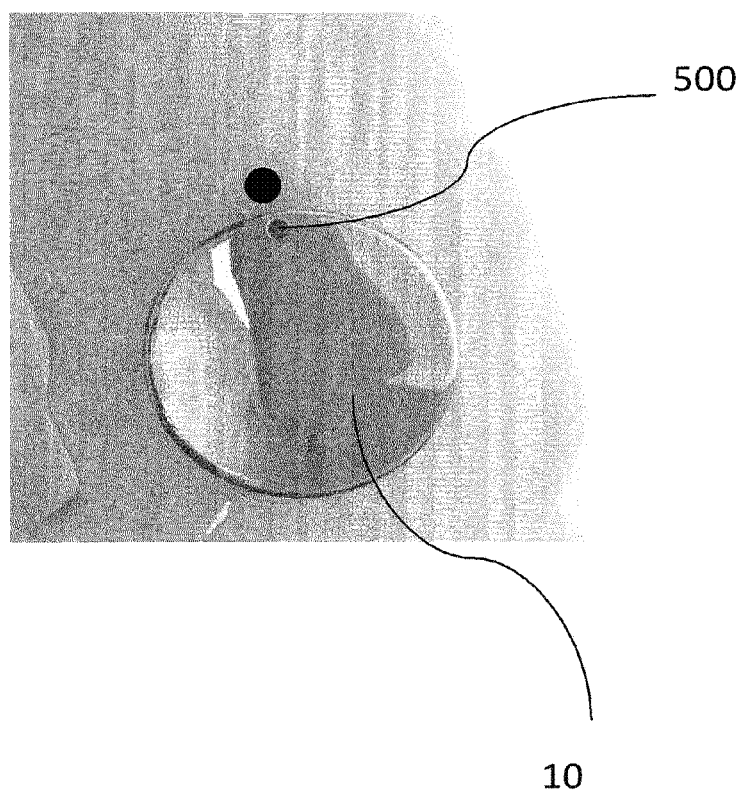
FIG. 11 shows a medical implant comprising a positioning mark according to the invention and wherein the direction of the positioning mark of the implant also is indicated on the cartilage surface due to previous guidance using the guide tool according to the invention during surgery.

FIG. 11 shows a medical implant comprising a positioning mark according to the invention and wherein the direction of the positioning mark of the implant also is indicated on the cartilage surface due to previous guidance using the guide tool according to the invention during surgery.

The present invention concerns a guide tool 12 which is designed to comprising a cartilage contact surface 52 which is individually designed to correlate to a surface and curvature in the joint. Due to this the guide tool 12 according to the invention may be correctly placed in the joint in one predetermined direction. The direction is determined during the design of the guide tool 12.

This predetermined direction may now be easier to visually see for the surgeon when he receives a guide tool according to the invention, designed to have a predetermined positioning mark, indicating a predetermined position instructing the surgeon about how he should place the guide tool 12 on the cartilage surface in the joint.

I. Determining Physical Parameters for a Cartilage Damage in a Joint.

An image or a plurality of images representing a three dimensional image of a bone member of the joint in a patient's limb may be obtained by a selected one of a per se known imaging technology for non-invasive imaging of joints, such as magnetic resonance imaging (MRI), computerized tomography (CT) imaging or a combination of both, or other suitable techniques such as delayed Gadolinium-enhanced MRI of cartilage (dGEMRIC) techniques. The image of the joint should comprise a representation of cartilage in the joint as well as the underlying subchondral bone in the area of the cartilage damage. Image data making up a three dimensional image representation of the joint is stored in a digital format in a manner that enables to keep track of the dimensions of the real joint that the image depicts.

The image data is analyzed in a data processing system to identify and determine physical parameters for the cartilage damage. The physical parameters to determine comprise the presence, the location and the size and shape of the cartilage damage, as well as curvature of the surface contour of the cartilage or the subchondral bone in an area of the cartilage damage.

In one embodiment of the inventive concept the design system operates to determine physical parameters on images of the patient's individual joint and the current cartilage damage, and thereby produces an individually designed guide tool 12. In another embodiment the design system operates on a collection of images of joints constituting a statistical basis for determining physical parameters for producing a guide tool 12 adapted for a selected location and a selected size of cartilage damage in a joint of a selected size.

The following steps, not limiting the design method according to the invention are in one exemplifying embodiment comprised in determining the physical parameters of cartilage damage:

a. Obtaining image data representing a three dimensional image of a bone member of the joint. By way of example, a sample of a set of several images which together represents a three dimensional image of a joint.

b. Identifying in the image data cartilage damage in an articulating surface of the bone member. In an automated process a computer program may be adapted to scan the image data for predetermined characteristics of a spot of cartilage damage in the image data. In a process with a manual part in this step an operator would visually scan a displayed image of the joint and identify a spot that has the visual characteristics of cartilage damage.

c. Determining based on the image data the location of the cartilage damage.

A set of data that represents a position of the cartilage damage in the joint is selected automatically or manually. The position data is for example stored as a set of defined coordinates in the image data.

d. Determining based on the image data the size and shape of the cartilage damage.

Selected measurements for size and shape of the cartilage are calculated in the image date, for example by determining a boundary line for the healthy cartilage surrounding the cartilage damage. A circular cross-section shape is preferably selected such that it covers the cartilage damage with a perimeter at a predetermined safe distance from the fringes of the damaged cartilage.

The size and shape data is for example stored as a set of perimeter and thickness data with a predetermined resolution.

e. Determining based on the image data the surface contour curvature of the cartilage and/or the subchondral bone in the joint in a predetermined area comprising and surrounding the site of cartilage damage.

The curvature of the surface contour is determined for example by per se known surface matching methods in image processing. The determined curvature information can be represented as an equation or as a set of image data. The determined curvature preferably comprises two subsets of curvature information. Firstly, one subset comprises the curvature of the contour portion that comprises the cartilage damage within the cross-section shape defining the selected boundary line for the area covering the cartilage damage. Secondly, the second subset comprises the curvature of a contour portion that surrounds the site of cartilage damage, preferably comprising mutually opposing sloping parts.

II. Generating Design Parameters for a Medical Implant (10).

Based on the physical parameters for the cartilage damage, design parameters for an implant are generated by processing the physical parameters in a design stage 95 according to a predetermined scheme for the shape of an implant in the specific surgical application.

The shape and size of the implant are calculated or selected dependent on the size and shape of the cartilage damage, and dependent on the curvature of the contour of the cartilage and/or of the subchondral bone in the area substantially coinciding with the cartilage damage, optionally a positioning mark is added to the articulating surface of said implant which indicate rotational positioning to the surgeon. The positioning mark 500 of the implant 10 may for example point out a direction in relation to the joint axis 501 or other anatomic dependent direction and may point out same direction as the positioning mark on the guide tool 12 used for placing said implant.

The following steps are in one non limiting exemplified embodiment of the design method of the invention comprised in generating design parameters for a medical implant 10:

f. Generating the contour curvature for an articulating surface of an implant body 27 dependent on said determined surface curvature of the cartilage and/or the subchondral bone.

The contour curvature for the articulating surface of the implant body is generated to correspond to the curvature that covers the cartilage damage.

g. Generating a cross-section for the implant body dependent on and substantially corresponding to said determined size and shape of the damaged cartilage.

The cross-section for the implant body is generated to correspond to the cross-section shape determined for the cartilage damage.

h. Generating an edge height 14 for the implant body that substantially corresponds to the thickness of healthy cartilage plus a selected height of a bone contacting part of the implant for countersinking the implant into a recess to be made in the bone to fit and receive the implant.

A first part of the edge height 14 for the implant body 27 is generated to correspond to the determined height of the healthy cartilage, and a second part corresponds to a countersink height selected automatically according to a predetermined scheme or selected manually by an operator.

i. Optionally generating a length and a cross-section profile for an extending post 23 extending from a bone contacting surface of the implant dependent on predetermined rules related to the size and shape of the cartilage damage.

The size and shape of the extending post is selected automatically according to a predetermined scheme or is selected manually by an operator.

The image based tool may also be configured for using predetermined shapes that are adapted to the determined physical parameters to automatically or manually fit to the cartilage damage and thereby generate the design parameters.

Generating design parameters for a guide tool 12 for implanting the implant.

The design parameters for the guide are generated dependent on the physical parameters for the cartilage damage and/or dependent on the design parameters for the medical implant.

The following steps are in one exemplified embodiment of the invention comprised in generating design parameters for a medical implant:

j. Generating the contact points for a cartilage contact surface 50 of a positioning body 11 dependent on said determined surface contour curvature of the cartilage and/or the subchondral bone in the joint in a predetermined area comprising and surrounding the site of cartilage damage, such that said cartilage contact surface 50 of the positioning body corresponds to and fits to said surface contour of the cartilage or the subchondral bone in the joint.

k. Generating the cross-section profile for a guide channel 54 in a guide body 13 extending from the positioning body, said guide channel 54 passing through said positioning body 11 and said guide body 13, the cross-section profile for the guide channel being generated dependent on and substantially corresponding to said determined size and shape of the damaged cartilage, and such that the guide channel 54 is designed to have a cross-sectional profile that corresponds to the cross-section of the plate shaped implant body 27, and such that the guide channel 54 is designed to have a muzzle 29 on the cartilage contact surface 50 of the positioning body at a position corresponding to the site of the diseased cartilage.

In further exemplifying embodiments inserts tools intended to be used inside the guide channel 54 may comprise positioning marks pointing in same direction as positioning mark on the guide tool 12;

Comprising of generating the cross-section profile for an insert tool to have a cross-sectional profile that corresponds to the cross-sectional profile of the guide channel 54 with a tolerance enabling the insert tool 8 to slide within the guide channel 54 further comprising a positioning mark pointing in same direction as the positioning mark on the guide tool 12.

Further Exemplified Embodiments of Design of Insert Tools;

Embodiments of the invention further comprise optional combinations of the following:

Generating design parameters for a drill bit 2 dependent on the design parameters for the extending post and such that a cross-sectional area for a drill bit is slightly smaller than the cross-sectional area for the extending post 23. Wherein the drill bit 2 is designed to comprise positioning marks pointing in same direction as the positioning mark present on the guide tool 12.

Generating design parameters for a cartilage cutting tool 6, 105 with a cross-sectional profile that is designed to correspond to the cross-sectional profile of the guide channel 54 with a tolerance enabling the cartilage cutting tool 6, to slide within the guide channel 54. Wherein the cutting tool is designed to comprise positioning marks pointing in same direction as the positioning mark present on the guide tool 12 indication in which rotational direction the cartilage cutting tool 6 should enter the guide channel 54 of the guide tool 12.

Generating design parameters for the implant comprises generating design parameters for an implant body 27 of the implant 10 being substantially flat, having a thickness 14 of approximately 0.5-5 mm.

Generating design parameters for the positioning body comprises generating design parameters for the cartilage contact surface of the positioning body having three contacting points 40, 42, 44, spread out around the guide body 13, for contacting parts of the joint in order to provide stable positioning of the guide tool 12 in the joint. Optionally designing the placement of the positioning mark on top said positioning body, so that the surgeon easily may see the mark during usage of the guide tool and wherein the positioning mark may point out a direction for placement of the guide tool in the joint in relation to the joint axis 501 or other anatomic dependent direction and may point out same direction as the positioning mark on the guide tool 12 used for placing said implant.

Generating design parameters for the guide channel 54 to have a height 31 of 3-10 cm.

Generating design parameters for the guide channel comprises generating design parameters for an orifice leading through the guide body 13 at the foot of said guide body.

Generating design parameters for a hammer tool 35 with a cross-sectional profile that is designed to correspond to the cross-sectional profile of the guide channel 54 with a tolerance enabling the hammer tool 35 to slide within the guide channel 54.

Details of the Surgical Kit

The Implant Structure

Figure 3A:
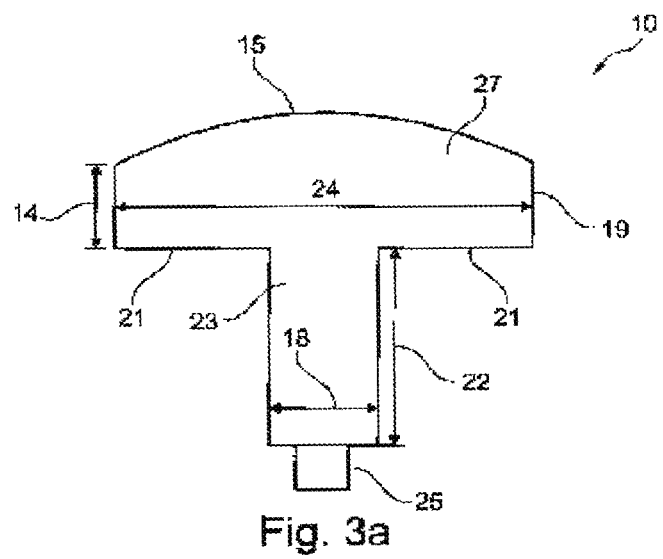
FIG. 3a-3b. Shows a medical implant according to the invention
Figure 3B:
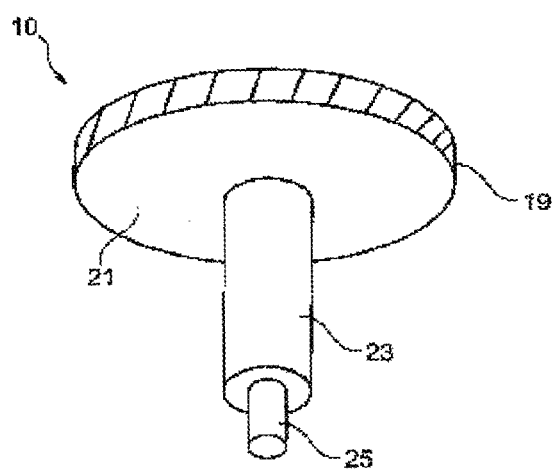

FIG. 3a-3b shows a medical implant 10 of a surgical kit according to an embodiment of the inventive concept. The plate shaped implant body 27 has an articulating surface (first surface) 15 configured to face the articulating part of the joint and a bone contact surface (second surface) 21 configured to face bone structure in the joint, the plate shaped implant body 27 has a cross-section that substantially corresponds to the area of the damaged cartilage and the articulating surface 15 has a curvature that substantially corresponds to the curvature of a healthy articulating surface at the site of diseased cartilage. The extending post 23 extends from the bone contact surface 21. Since the implant 10 of the inventive concept is custom made for a specific patient, FIG. 3a-b is an exemplifying schematic picture displaying one embodiments of the implant 10. Between the articulating surface 15 and the bone contact surface 21 there is a cartilage contacting surface 19.

The implant is specially designed, depending on the knees appearance and the shape of the damage and in order to resemble the body's own parts, having a surface which preferably corresponds to a three dimensional (3D) image of a simulated healthy cartilage surface. The implant will be tailor-made to fit each patient's damaged part of the joint.

Implant Body

The implant body 27 is substantially plate shaped, meaning that the shortest distance (represented by 24 in FIG. 3) crossing the surface 15 of the implant body 27 is substantially larger, e.g. at least 1.5 times larger than the thickness 14 of the implant body 27. By substantially plate shaped is meant that the implant body 27 may be substantially flat or may have some curvature, preferably a 3D curvature of the articulating surface 15. The articulating surface 15 may for example have a curvature that corresponds to a simulated healthy cartilage reconstructed from an image taken e.g. with MRI or CT-scanning of the damaged cartilage surface of the joint. Once the implant 10 is placed in the joint there will be a surface with no parts of the implant pointing up from or down below the surrounding cartilage—the implant is incorporated to give a smooth surface.

The area and the shape of the implant surface 15 are individual depending on the size of cartilage damage and location of the cartilage damage. The area and shape of the implant can be decided by the surgeon himself or be chosen from predetermined shapes. For instance the cross-section of the implant body 27 may have a circular or roughly circular, oval, triangular, square or irregular shape, preferably a shape without sharp edges (see FIG. 8 a-b and implant 10). The implant head or implant body 27 can vary in size and shape and are adjusted to the size and shape of the damaged cartilage tissue and to the needs of particular treatment situations. The size of the implant 10 may also vary. The area of the articulating surface 15 of the implant varies in different realizations of the inventive concept between 0.5 $cm^2$ and 20 $cm^2$, between 0.5 $cm^2$ and 15 $cm^2$, between 0.5 $cm^2$ and 10 $cm^2$, between 1 $cm^2$ and 5 $cm^2$ or preferably between about 0.5 $cm^2$ and 5 $cm^2$.

In general, small implants are preferred since they have a smaller impact on the joint at the site of incision and are also more easily implanted using arthroscopy or smaller open surgical procedures. The primary factor for determining the size of the implant is however the nature of the lesion to be repaired.

The Extending Post

The implant replaces an area of damaged cartilage in an articulating surface of a joint. Before the implant is placed in the desired position, the damaged cartilage is removed and also a part of the bone beneath, i.e. a recess fitting the implant is made in the bone. Furthermore, a hole can be drilled in the bone to fit the implant structure. The extending post of the implant or the rod-part 23 of the implant 10, is used for securing the implant 10 in the drilled hole of the bone. The length 22 of the extending post 23, extending from the implant head 27, is adjusted to a length needed to secure the implant 10 in the bone. The extending post 23 is intended to give a primary fixation of the implant 10, it provides mechanical attachment of the implant 10 to the bone in immediate connection with the surgical operation.

The position of the extending post 23 on the bone contact surface 21 can be anywhere on the bone contact surface 21 or the extending post 23 may have a central position.

The extending post 23 has a physical structure in the form of for example a cylinder or other shapes such as one or more of a small screw, peg, keel, barb or the like.

In one embodiment, the extending post 23 has a positioning part 25, where the positioning part 25 is located distal to the plate shaped implant body 27. The longitudinal symmetry axes of the first part of the extending post 23 and the positioning part 25 coincide. The diameter of the positioning part 25 is smaller than the diameter of the first part of the extending post 23.

The Guide-Tool

Figure 13A:
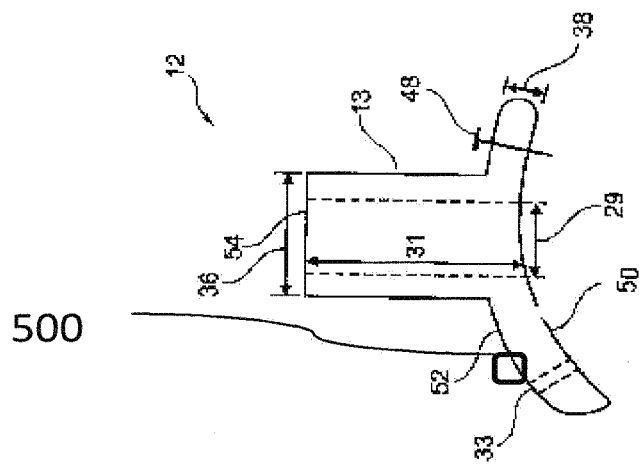
FIG. 13a-b shows exemplified embodiments of the guide tool according to the invention.
Figure 13B:
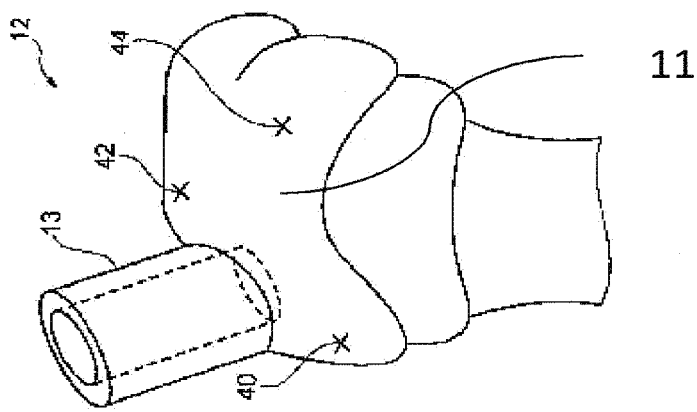

FIG. 13a-b shows exemplifying embodiments of a guide-tool 12. Other examples of guide tools according to the invention is The guide tool 12 comprises a positioning body 11 and a guide body 13, with a guide channel 54 through said guide body 13 and positioning body 11. The positioning body has a cartilage contact surface 50 that has a shape and contour that is designed to correspond to and to fit the contour of the cartilage or the subchondral bone in the joint in a predetermined area surrounding the site of diseased cartilage. The guide tool 12 also has a top surface 52 facing the opposite direction compared to the cartilage contacting surface 50. The guide body 13 extends from said top surface 52 of the guide tool 12.

The guide channel 54 has an inner cross-sectional profile that is designed to correspond to the cross-section of the plate shaped implant body 10. In other words, the plate shaped implant body 10 fits the guide channel 54, with a slight tolerance to allow a sliding movement of the implant in the guide channel 54. The positioning body 11 has a mouth or muzzle 29 which is the guide channel's 54 opening on the cartilage contact surface 50. The mouth 29 is in a position on the cartilage contact surface 50, corresponding to the site of the diseased cartilage in a joint. The height 31 of the guide channel 54 must be sufficiently long to give support to the tools used inside the guide body 13. The height 31 is preferably higher than the thickness of the surrounding tissue. In this way, the opening of the guide channel 54 is easy to access for the surgeon. The height 31 of the guide channel 54 is between 1 and 10 cm, preferably 3-10 cm, and always sufficiently high to ensure stabilization of the tools that are to be inserted into the guide channel 54.

The guide tool 12 is easy to place due to the precise fit of the positioning body 11 on the cartilage surface. The guide tool 12 is designed to be inserted in as lesion which is as small as possible to be able to repair the specific cartilage damage. The height 31 of the guide channel 54 is sufficiently high to be easily accessible for the surgeon during surgery. In one embodiment, the top of the guide channel 54 is designed to project above the tissue surrounding the surgery cut when the guide tool is placed on the cartilage in a joint during surgery.

The size and shape of cartilage contact surface 50 of the guide tool 12 is determined depending on the size and shape of the damaged cartilage and thus on the cross section of the implant body 10 and the guide channel 54, and also depending on the position of the cartilage area in a joint. The size, shape or spread of the surface 50 is a consideration between the following aspects; minimize surgery lesion, maximize stability for guide tool 12, anatomic limitations on the site of the injury. Not all cartilage surfaces in a joint can be used for placement of the guide tool. A large spread of the cartilage contact surface 50 is to prefer to get good stability of the guide tool, however, a large surface area of the surface 50 may also lead to a large surgical intervention which is undesired. Thus the size of the cartilage contact surface 50 and of the positioning body 13 is determined by a balance between the desire to achieve good positioning stability and small surgical operations. Also, the cartilage contact surface 50 need not have a continuous, regular shape, but may have an irregular shape, as long as it gives adequate support and stable positioning of the guide tool 12. The cartilage contact surface may also consist of three separated points.

When designing the guide tool, the cartilage contact surface 50 can be designed to cover three points (40, 42, 44 for an example, see FIG. 13b) distributed over the cartilage surface of the joint where the implant is to be inserted. The points are chosen to give maximum support and positional stability for the positioning body 11 and thus these points, either decided and identified by the surgeon or automatically identified by design software, serve the ground when designing the surface 50 of the guide tool 12. The cartilage contact surface 50 can also be formed such that it uses the curvature in the cartilage surface in a joint for stability. For example, in a knee joint, the condyles are separated from each other by a shallow depression, the posterior intercondyloid fossa, this curvature together with the medial epicondyle surface can be used to give the cartilage contact surface 50 a stabile attachment to the cartilage surface in a knee joint. The cartilage contact surface does not need to be a continuous, regular surface but preferably has the three points exemplified by 40, 42 and 44 for stability. Optionally the cartilage contacting surface 50 can be further stabilized by attachment with nails, rivets or similar attachment means to the bone surrounding the cartilage in a joint (see FIG. 4b). This additional attachment with rivets 48 or the like gives additional support and stability and also gives the possibility to keep the cartilage contact surface as small as possible. The position of the rivets may be predetermined and marked out on the surface 50 by premade drill holes 33.

The guide-tool 12 aids with exact precision removal of a volume of cartilage and subchondral bone and the guide tool 12 also guides the placement of the implant 10 in for example a knee. Placement of an exemplified embodiment of the guide-tool 12 on the cartilage surface on a knee can be seen in FIG. 13a.

The guide body 13 comprises an orifice, see FIG. 11, at the foot of the guide body that leads from the guide channel into the open outside the guide body. The orifice 145 is designed to enable output of waste such as cartilage tissue and bone chips from boring or reaming in the preparation of the recess for the implant in the joint. The orifice is preferably also designed to enable visual inspection into the implant site during surgical operation.

The guide tool according to the present invention is further designed to comprise a positioning mark 500, comprised in the structure of the positioning body or guide body or guide channel construction of the guide tool and wherein the positioning mark is aligned with the center 503 of the guide channel 54 in a chosen joint axis 501 direction.

Figure 7:
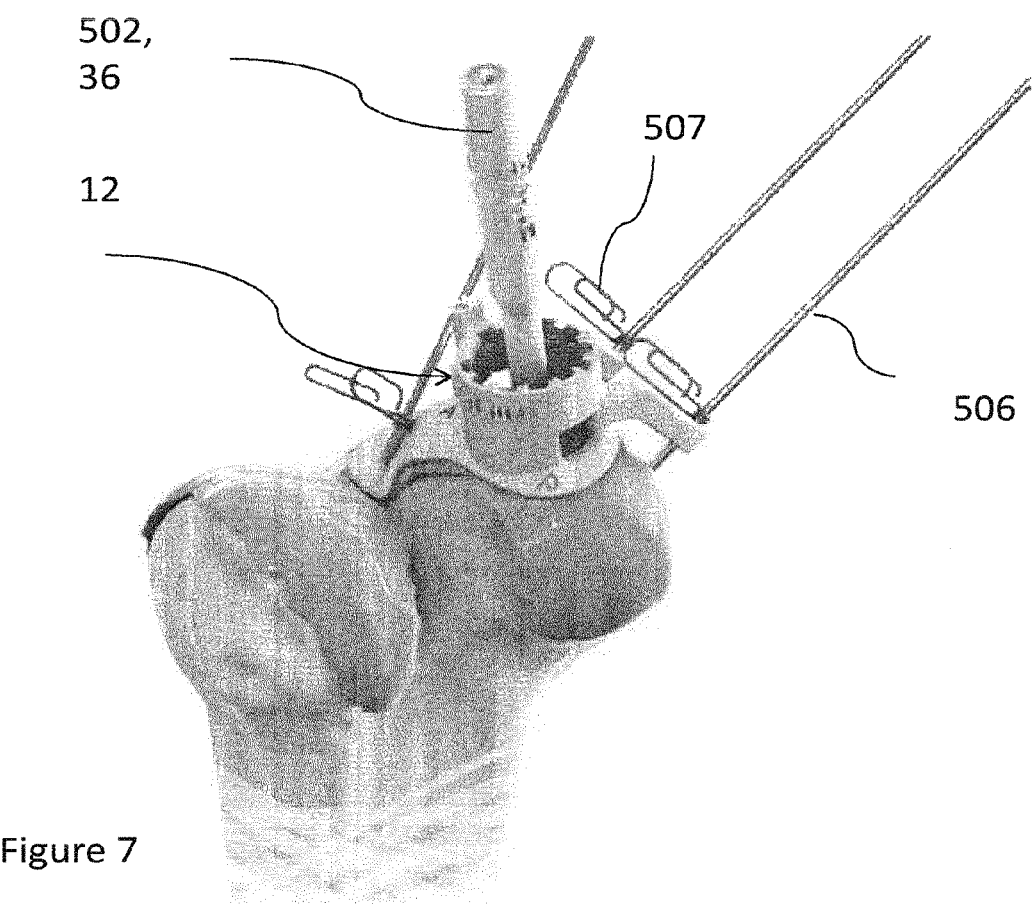
FIG. 7 shows a guide tool according to the invention placed on the cartilage in a joint and further comprising an implant dummy insert tool 36 placed in start position inside the guide channel 54, and wherein the positioning mark 500 of the guide tool 12 and the positioning mark 500 of the implant dummy 36 are aligned and the positioning mark on the implant dummy is placed on top of the implant dummy shaft.

The guide tool 12 may be placed in the joint using pins 506 and clamps 507 for stabilization and fastening see for example in FIG. 7.

The Insert Tool 502

The insert tool 502 is in different embodiments of the invention for example selected from; the cartilage cutting tool, the punch, the cartilage cut drill, the reamer guide, the drill guide or the hammer tool, implant dummy, cartilage cutter. The insert tool is used inside the guide channel 54 of the guide tool 12 and fits in the guide channel 54, with a slight tolerance to allow a sliding movement of the insert tool in the guide channel 54. The cross-sectional profile, and thus the circumferential shape of the insert tool, corresponds to the chosen cross-section of the implant surface 15 in size and shape The Cartilage Cutting Tool The cartilage cutting tool is a tool which is used to cut the cartilage in the joint around the area of damaged cartilage to prepare for the insertion of the implant. The cartilage cutting tool may for example be a punch 6 or a cartilage cut drill 105. It is used inside the guide channel 54 of the guide tool 12 and fits in the guide channel 54, with a slight tolerance to allow a sliding movement of the cartilage cutting tool in the guide channel 54. The cartilage cutting tool preferably cuts the cartilage so that the cut edges of the cartilage are sharp and smooth. These sharp and smooth edges are of great importance when the implant is placed into the prepared recess in the cartilage and bone. In one embodiment the cartilage cutting tool, in addition to cutting the cartilage, may also cut/carve/drill the underlying bone. A hole in the cartilage which is cut (punched or drilled) with the cartilage cutting tool according to the inventive concept ends up with a precise fit of the implant into the prepared cartilage since the cartilage cutting tool allows for an exact, precise cut. The recess in the cartilage and/or bone, made by the cartilage cutting tool always correspond to the chosen cross-section of the implant surface 15 in size and shape In one exemplifying embodiment of the inventive concept the cartilage cutting tool is a punch 6. The punch 6 is a solid body with a hollow shape or recess 5 in one end. The recess 5 has sharp edges 60. The punch 6 is used to punch out and remove the damaged cartilage from the joint. The punch is to be placed inside the guide channel 54 of the guide tool 12, with the recess pointing down onto the cartilage. A hammer is then used to hammer the punch recess 5 through the cartilage. In this way the damaged cartilage is removed by punching. The depth 59 of the recess 5 on the punch 6 may be adjusted to the individual person's cartilage thickness. It is of great importance that the punch has sharp cutting edges 60.

The punch 6 fits the inside of the guide channel 54, with a slight tolerance to allow a sliding movement of the punch in the guide channel 54. The fit ensures the correct, desired placement of the punch on the cartilage surface and thus the precise removal of the damaged cartilage area.

The punch preferably gives sharp precise edges of the remaining cartilage in the joint surrounding the removed cartilage piece, which is of importance when placing the implant 10 in the joint. The contour of the cutting edge 60, i.e. the contour of the surface of the cutting edge 60 that is to face and cut the cartilage, is in one embodiment designed to match the contour of the patient's cartilage and/or bone at the site of the joint where the punch is to cut. This further ensures that the cartilage will be properly and efficiently cut, giving sharp precise edges of the remaining cartilage as well as minimized damage to the underlying bone.

The length 56 of the punch 6 is in one embodiment longer than the height 31 of the guide channel 54. The length 56 of the punch 6 is preferably between 4 and 12 cm.

The cross-sectional profile, and thus the circumferential shape of the cutting edge 60, of the punch 6 corresponds to the chosen cross-section of the implant surface 15 in size and shape The cross-sectional profile of the punch varies in different realizations of the inventive concept between 0.5 $cm^2$ and 20 $cm^2$, between 0.5 $cm^2$ and 15 $cm^2$, between 0.5 $cm^2$ and 10 $cm^2$ or preferably between about 1 $cm^2$ and 5 $cm^2$.

In one exemplifying embodiment of the inventive concept the cartilage cutting tool is a cartilage cut drill. The cartilage cut drill is used to cut the cartilage in the joint around the area of damaged cartilage to prepare for the insertion of the implant with a cut-drill technique.

The cartilage cut drill 105 is a drill, with a drill body 111 and with sharp cutting edges 108 and a center marker 106. The cartilage cut drill 105 has a cross-sectional profile that is designed to correspond to the inner cross-sectional profile of the guide channel 54 with a tolerance enabling cartilage cut drill body 111 to slide within the guide channel 54. Also, the cross-sectional profile is designed to correspond to the cross-section of the implant.

The Reamer Guide

In one embodiment of the inventive concept the surgical kit comprises a reamer guide that is placed in the guide channel 54 before reaming the recess in the bone. The reamer guide placed in the guide channel 54 protects the cartilage surrounding the implant site while the reamer bit 4 is used inside the guide channel 54 of the guide tool 12.

The reamer guide 28, is a channel shaped structure with thin walls designed to fit the inside of the guide channel 54, with a slight tolerance to allow a sliding movement of the reamer guide 28 in the guide channel 54. In other words, the cross-sectional profile of the reamer guide 28 fits the cross sectional profile of the guide channel 54 such that the reamer guide 28 may be used as a lining, lining the insides of the guide channel 54 (see FIG. 8). The walls of the reamer guide 28 have a thickness of less than 1 mm. The reamer guide 28 preferably has a height 66 that is at least the height achieved by adding the inner height 31 of the guide channel 54 with the height 59 of the recess 5 of the punch 6.

The Height Adjustment Device or Insert Tool

A height adjustment device 16 according to the invention comprises a male part 47 and a female receiving part 48 which when used together allows for stepwise adjustment of drill depth.

The male part is in the outermost position in a zero-mode and may from there be adjusted inwards allowing the surgeon stepwise the for example make stepwise deeper drill holes. When the height adjustment device 16 is in starting mode or outermost zero-mode the positioning marking of the guide tool 12 and the positioning marking of the height adjustment device are aligned, se for example FIG. 6.

Thus, by being able to adjust the length 31 of the guide channel the surgeon is also able to adjust the depth of drilling and cutting into the bone. The length 31 of the guide channel may be varied since the guide body 13 and the height adjustment device 16 parts are able to move in relation to one another. Further, the male part 47 and the female receiving part 48 of the height adjustment device may be arranged such that the length 31 of the guide channel may be varied at certain stepwise intervals 115, e.g. at 200 μm or at 100-300 μm intervals or steps, or any other desired interval, see for example FIG. 16. For example, the height might be adjusted between for example 0.2-3 mm, in one or several steps. This may for instance be achieved by arranging the male part 47 inside the female receiving part 48 of the height adjustment device 16 such that the male part 47 insert tool to have a cross-sectional profile that corresponds to the cross-sectional profile of the female part guide channel 120 with a tolerance enabling the insert tool to slide within the guide female part guide channel 120. For example, the construction may be arranged such that the guide body 13 and height adjustment device 16 may be turned in relation to one another at preset steps, by lifting the male part sot that the protruding ridges may slip out of one groove and enter another groove. When the male part 47 is fitted in the female part their position are locked in relation to each other or prone to hook each other at those intervals. The female part comprises grooves or ledges 17 at different heights relative to the positioning body of the guide tool. The male part 47 comprises a guide channel 54 inside the male part 47, the guide channel 54 may be cylinder shaped and protruding ridges 105 on the outer surface of the male part 47. When the male part 47 is placed inside the female receiving part 48 the protruding ridges 105 of the male part 47 are placed or located inside one of the grooves 17 on the female receiving part 48. The position of the grooves 17 and the position of the ridges 105 in relation to the positioning body or the cartilage contact surface 50 adjust or regulate the length 31 of the guide body 13. The height adjustment device 16 may be used by the surgeon to adjust the depth of drilling, e.g. by increasing the drill depth in steps at the preset intervals. The height adjustment device 16 may advantageously be used together with an implant dummy 36, as described below, to make sure that the drill depth in the bone matches the height 14 of the implant body 27. This ensures that the articulating surface 15 of the implant 10 will be in line with the surrounding cartilage at the site of implantation once implanted.

The Drill-Guide,

In one embodiment of the inventive concept the surgical kit comprises a drill guide 8 that is used to direct a drill for drilling a hole in the bone at the site of cartilage damage, for fastening of the extending post 23 of the implant 10 in the bone tissue. The drill guide 8 comprises a drill guide body and a guide channel 7 passing through the drill guide body. The guide channel 7 is designed to receive and guide the drill during the surgical procedure. The drill guide 8 is designed to fit the inside of the guide channel 54, with a slight tolerance to allow a sliding movement of the drill guide 8 in the guide channel 54, see FIG. 8a-b. In other words, the cross-sectional profile of the drill guide body matches the cross-sectional profile of the guide channel 54 The fit ensures the correct, desired placement of the drill guide 8 on the cartilage surface and thus ensures the precise direction and placement of the drill hole in the bone.

The guide channel 7 is designed to be positioned in the drill guide body such that the position corresponds to the desired position of the drill hole in the bone. The positioning of the guide channel 7 in the drill guide 8 is coordinated with the positioning of the extending post 23 on the bone contacting surface 21 of the implant to ensure correct positioning of the implant in the bone.

The length 62 of the drill guide 8 and thus the drill channel 7 is longer than the height 31 of the guide channel 54. The length is preferably 4-12 cm.

The cartilage contacting surface 64 of the drill guide 8 corresponds to the chosen implant surface 15 in size and shape. The surface 64 varies in different realizations of the inventive concept between 0.5 cm$^2$ and 20 cm$^2$, between 0.5 cm$^2$ and 15 cm$^2$, between 0.5 cm$^2$ and 10 cm$^2$ or preferably between about 1 cm$^2$ and 5 cm$^2$. In one embodiment the cartilage contacting surface 64 of the drill guide 8 is designed to match the contour of the patient's cartilage and/or bone at the site of the joint where the implant is to be inserted.

See FIG. 9c for a demonstration of how the drill-guide 8 fits inside the guide-channel 54 of the guide-tool 12.

Drill-Bit

Figure 12:
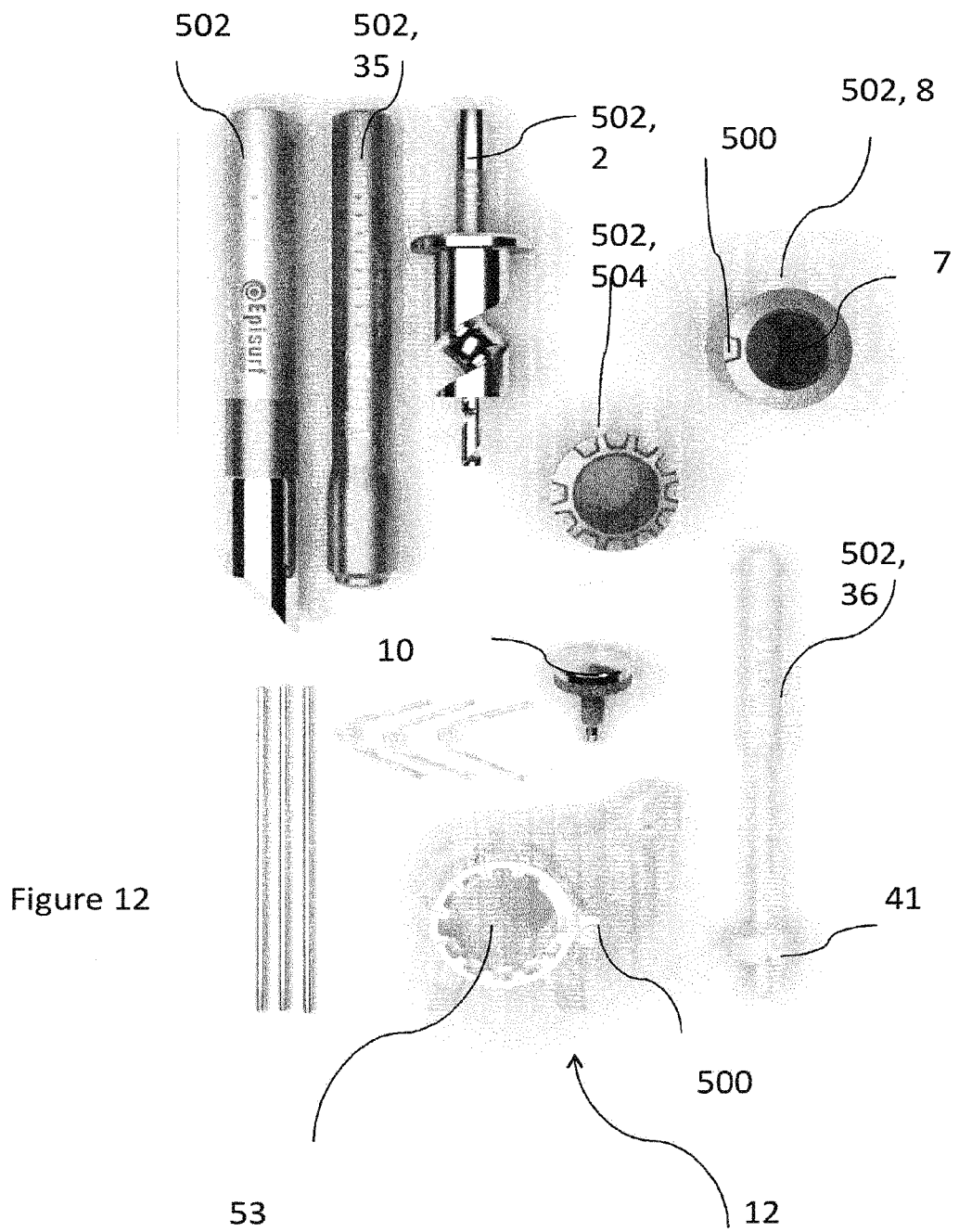
FIG. 12 shows an exemplified embodiment of a guide tool and insert tools and implant designed using the design method according to the present invention.

The surgical kit of the present inventive concept may also comprise a drill-bit 2, see FIG. 12. The drill-bit 2 may have an adjustable depth gauge 1. The depth gauge 1 on the drill-bit 2 is supported by the top 30 of the guide channel 54 and by using this support the depth of the drill hole can be controlled. The drill-bit 2 fits inside the drill channel 7 in the drill-guide 8 to give a drill-hole in the bone with an exact position and depth and where the depth is depending on the placement of the depth gauge 1 on the drill-bit 2, and also depending on the height of the guide-channel 31.

Reamer-Bit

The surgical kit of the present inventive concept may also comprise a reamer-bit. The reamer-bit 4 may have a depth gauge 3. The reamer bit 4 is used together with the guide-tool 12 and possibly the reamer guide 28. The reamer-bit 4 is used inside the guide channel 54, removing bone tissue, aided by the guide channel 54 and possibly the reamer guide 28. The depth gauge 3 on the reamer-bit 4 is supported by the top 30 of the guide channel 54 and by using this support the depth of the reamed bone recess can be controlled. The depth of the reamed recess in the bone is depending on the placement of the depth gauge 3 on the reamer-bit 4, and also depending on the height 31 of the guide-channel 54. The depth of the reamed surface is determined depending on the injury and on the desired implants size.

Hammer Tool

Figure 8:
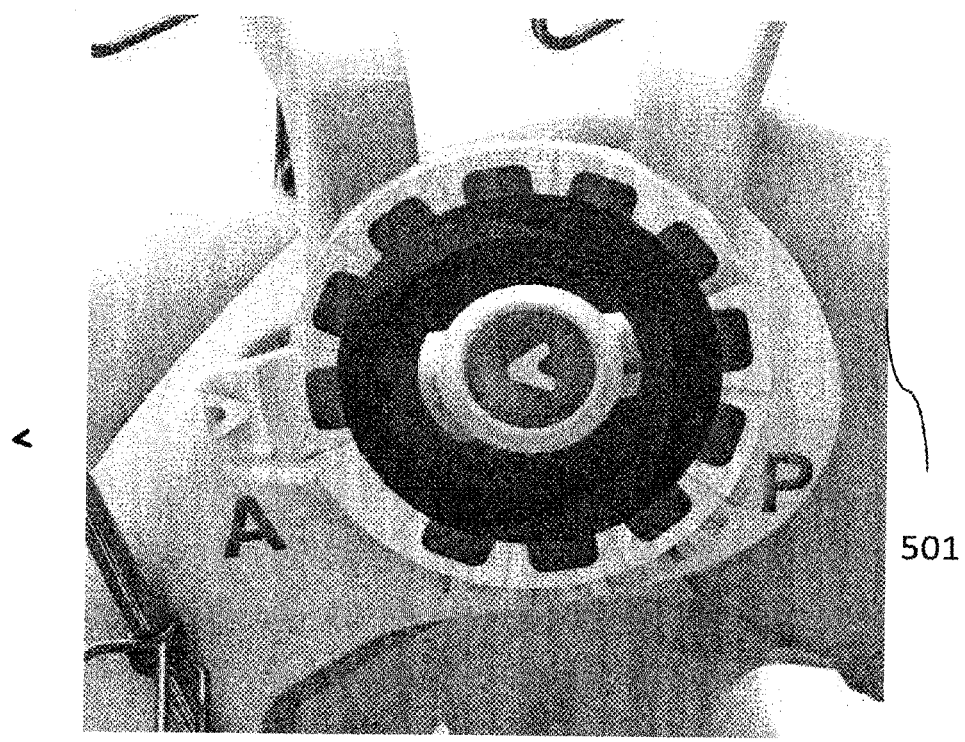
FIG. 8 shows another view of a guide tool according to the invention placed on the cartilage in a joint and further comprising an implant dummy insert tool placed in start position inside the guide channel, and wherein the positioning mark of the guide tool and the positioning mark of the implant dummy tool are aligned and the positioning mark on the implant dummy is placed on top of the implant dummy shaft.
Figure 9:
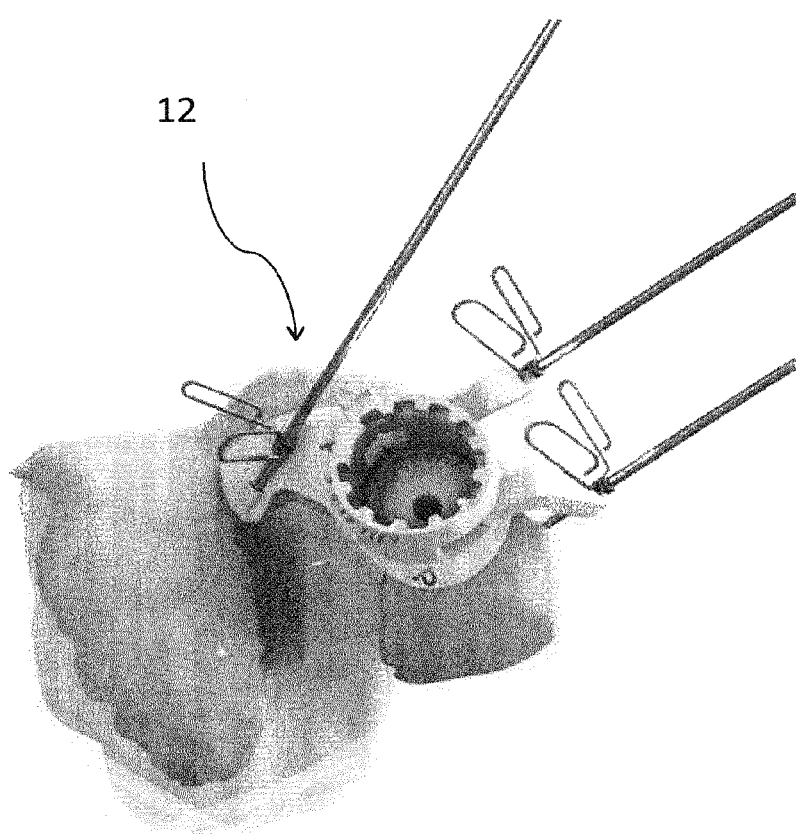
FIG. 9 shows a guide tool according to the invention placed on the cartilage in a joint and further showing a view how it looks like when the height adjustment tool 504 has been used inside the guide channel together with a reamer and/or drill to make a recess in a desired size and depth wherein the implant according to the invention can be placed.
Figure 10:
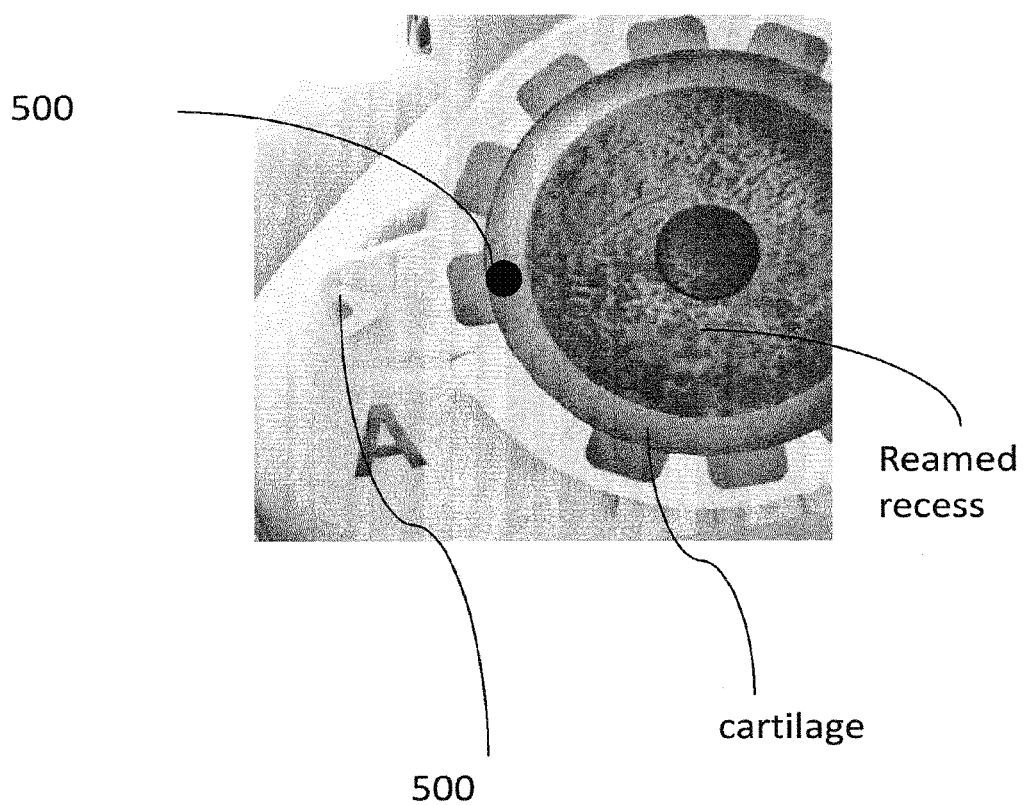
FIG. 10 shows a guide tool according to the invention placed on the cartilage in a joint and further showing how the positioning mark of the guide tool is used to make a mark on side of the recess wherein the implant is to be placed in order to know in which direction the implant is to be placed in the recess when the guide is removed before placing the implant in the joint.

The optional hammer tool 35 (see FIG. 12) consists of a solid body and is designed to fit the inside of the guide channel 54, with a slight tolerance to allow a sliding movement of the hammer tool 35 in the guide channel 54, see FIG. 8. The hammer tool 35 is used inside the guide channel 54 to hammer the implant in place. The height of the hammer tool 68 is the same height 62 as of the drill guide 8. Once the hammer tool is hammered in the same level as the top of the guide channel, the hammering and thus the placement of the implant is finished.

Implant Dummy and Dummy Reference

The implant dummy 36 and dummy reference 37, see FIG. 12, are used to make sure that the cut, carved or drilled recess in the bone that is to receive the implant body 27, is deep enough to fit the implant. This is very important, since the articulating surface 15 of the implant 10 must not project over the surface of the surrounding cartilage tissue. If it would it could cause a lot of damage to the surrounding cartilage and to the cartilage on the opposite side of the joint. Preferably the articulating surface 15 should form a continuous surface with the surrounding cartilage, neither projecting above nor being sunken below the surface of the surrounding cartilage. The checking of the recess depth is difficult or impossible to do with the implant 10 itself, since the implant 10, e.g. with its extending post 23, is designed to be fixed in the bone once inserted, and thus is difficult or impossible to remove. The implant dummy, on the other hand, is designed for easy removal from the recess once the recess depth has been checked.

The implant dummy 36, see FIG. 12, has an implant element 41 that is designed to match the implant body 27. The lower surface 41a of the implant element 41 is a replica of the bone contact surface 21 of the implant that is to be implanted. That is, if the implant 10 and bone contact surface 21 is custom made for the specific patient, the implant element 41 and its lower surface 41a will also be custom made and the lower surface 41a be a replica of the bone contact surface. The cross-sectional profile of the implant element 41 corresponds to the cross-sectional surface of the implant body, or is slightly smaller in order to ensure easy removal of the implant dummy from the recess.

The implant dummy 36 also has a top surface. The distance between the lower surface of the implant element 41 and the top surface corresponds to the distance that you get when adding the thickness 14 of the implant body 27 (corresponding to the depth of the recess in the bone plus the thickness of the corresponding cartilage). The dummy reference 37, see FIG. 12, is arranged to fit to, and possibly releasable attach to, the guide hole 53 of the guide base 12, see.

To ensure that the implant dummy 36 is placed in a correct orientation in the recess of the bone, i.e. in an orientation that corresponds to the orientation that the implant 10 is to be inserted in, the top surface 43 and/or the implant element 41 may be provided with positioning mark 500. A corresponding positioning mark 500 is provided also on the implant dummy 36 and on the guide base 12.

A Medical Implant Comprising at Least Two Substantially Circular Shapes

Figure 14A:
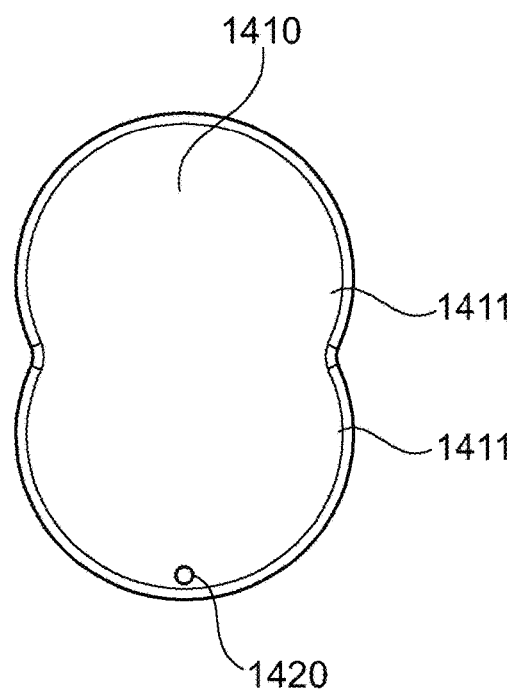
FIGS. 14a-b show a medical implant according to the invention which comprises two substantially circular shapes where one of the circular shapes is provided with a positioning mark on its articulating surface.
Figure 14B:
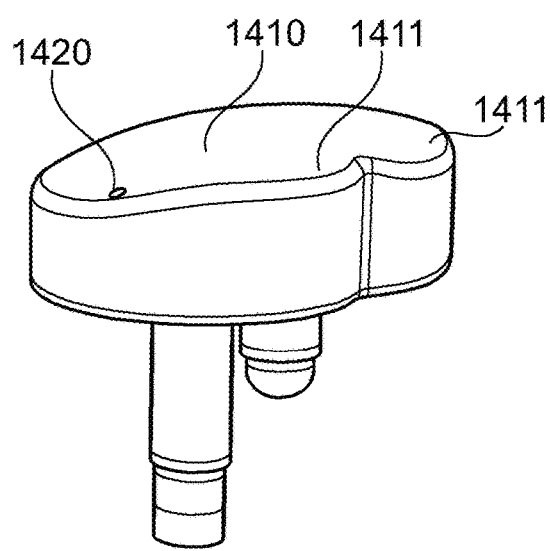

FIGS. 14a and 14b show a medical implant 1410 according to the invention which comprises two substantially circular shapes 1411 where one of the circular shapes is provided with a positioning mark 1420 on its articulating surface 15.

The positioning mark 1420 on the articulating surface 15, i.e. the top surface 15 facing the articulating part of the joint, of one of the circular shapes of the medical implant illustrated in FIGS. 14a and 14b is designed to be used for determining the orientation in which the implant is to be placed in a recess made in a damaged articulating surface of a joint.

The positioning mark 1420 on the articulating surface 15, i.e. the top surface 15 facing the articulating part of the joint, of one of the circular shapes of the implant illustrated in FIGS. 14a and 14b may be designed so that the direction of the positioning mark 1420 is determining the placement orientation of the implant in a recess in that the placement orientation of the positioning mark is also to be indicated by a mark made on the side of a recess made in the articulating surface of a joint in which the implant is to be inserted, thereby providing for a correct or more accurate orientation of the implant when inserted in the recess made in a damaged articulating surface of a joint.

The positioning mark 1420 on the articulating surface 15, i.e. the top surface 15 facing the articulating part of the joint, of one of the circular shapes of the implant 1420 illustrated in FIGS. 14a and 14b may be designed so that the direction of the positioning mark is designed to be pointing in an anatomic dependent direction in relation to a recess made in the articulating surface of a joint in which the implant is to be inserted, thereby providing for a correct or more accurate orientation of the implant when inserted in the recess made in a damaged articulating surface of a joint.

FIGS. 15a and 15b shows a medical implant 1510 according to the invention which comprises two substantially circular shapes 1511, e.g. designed from using a virtual model comprising two substantially circular shapes, where one of the circular shapes is provided with a positioning mark 1520 on its the cartilage contacting surface 19, i.e. its side edge surface 19.

The positioning mark 1520 on the cartilage contacting surface 19, i.e. the side edge surface 19, of one of the circular shapes of the medical implant illustrated in FIGS. 15a and 15b is designed to be used for determining the orientation in which the implant 1520 is to be placed in a recess made in a damaged articulating surface of a joint.

The positioning mark 1520 on the cartilage contacting surface 19, i.e. the side edge surface 19, of one of the circular shapes of the implant illustrated in FIGS. 15a and 15b may be designed so that the direction of the positioning mark 1520 is determining the placement orientation of the implant in a recess in that the placement orientation of the positioning mark is also to be indicated by a mark made on the side of a recess made in the articulating surface of a joint in which the implant is to be inserted, thereby providing for a correct or more accurate orientation of the implant when inserted in the recess made in a damaged articulating surface of a joint.

The positioning mark 1520 on the cartilage contacting surface 19, i.e. the side edge surface 19, of one of the circular shapes of the implant illustrated in FIGS. 15a and 15b may be designed so that the direction of the positioning mark is designed to be pointing in an anatomic dependent direction in relation to a recess made in the articulating surface of a joint in which the implant is to be inserted, thereby providing for a correct or more accurate orientation of the implant when inserted in the recess made in a damaged articulating surface of a joint.

Figure 16:
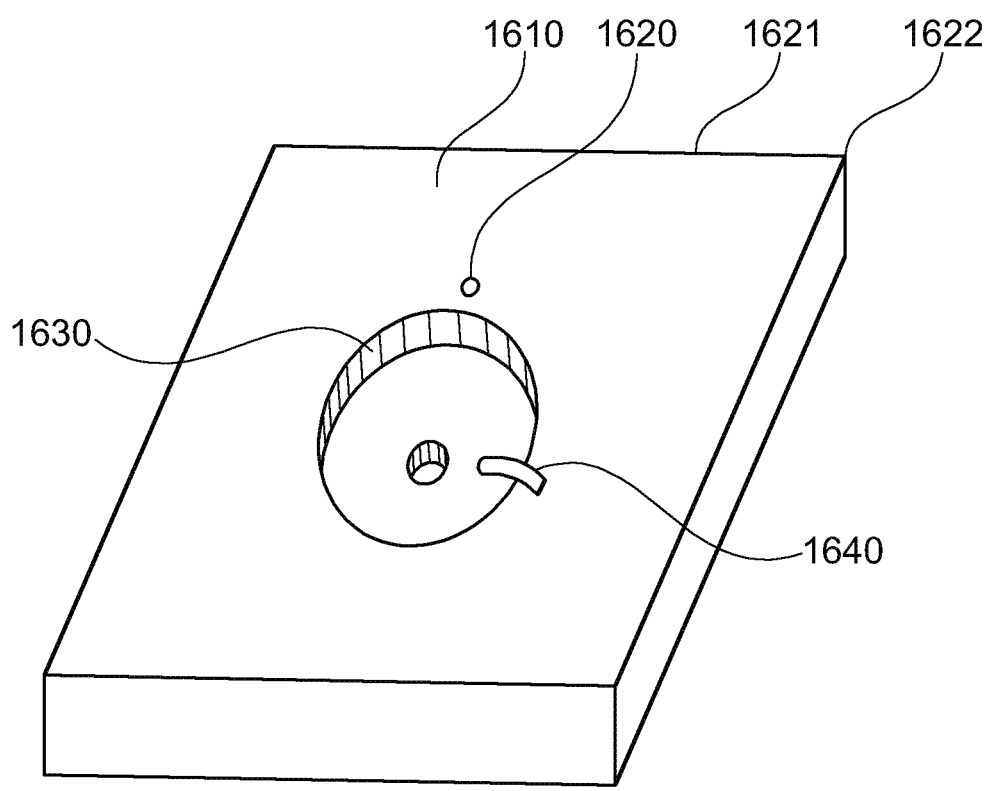
FIG. 16 shows a storage unit adapted for storing a medical implant of substantially circular shape prior to inserting the medical implant in a recess made in a joint.
Figure 16:
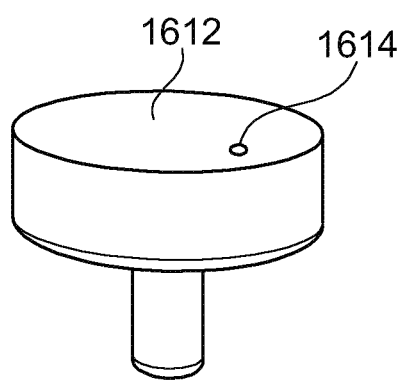

Storage Units for Storing a Medical Implant Prior to Inserting the Implant in a Human Joint FIG. 16 shows a storage unit 1610 adapted for storing a substantially circular shaped medical implant 1612 prior to inserting the medical implant in a recess made in a joint. The storage unit 1610 illustrated in FIG. 16 comprises a plurality of reference features in the form of a positioning mark 1620, an edge 1621 and a corner 1622.

The storage unit 1610 illustrated in FIG. 16 further comprises both a mechanical recess structure 1630 and holding means 1640 adapted for holding and positioning the implant 1612 in a rotationally fixed position in the storage unit 1610.

The plurality of reference features 1620, 1621, 1622 of the storage unit 1610 illustrated in FIG. 16 are adapted to be used for rotationally positioning the substantially circular shaped implant 1612 in the storage unit 1610 in that a positioning mark 1614 on the substantially circular shaped implant to be stored in the storage unit 1610 is used for rotationally positioning the implant 1612 in relation to the plurality of reference features 1620, 1621, 1622. The implant 1612 is then placed in the storage unit 1610 by directing the implant positioning mark 1614 on the surface of the implant in a specific, e.g. pre-determined, rotational direction in relation to at least one of the plurality of reference features of the storage unit.

Figure 17:
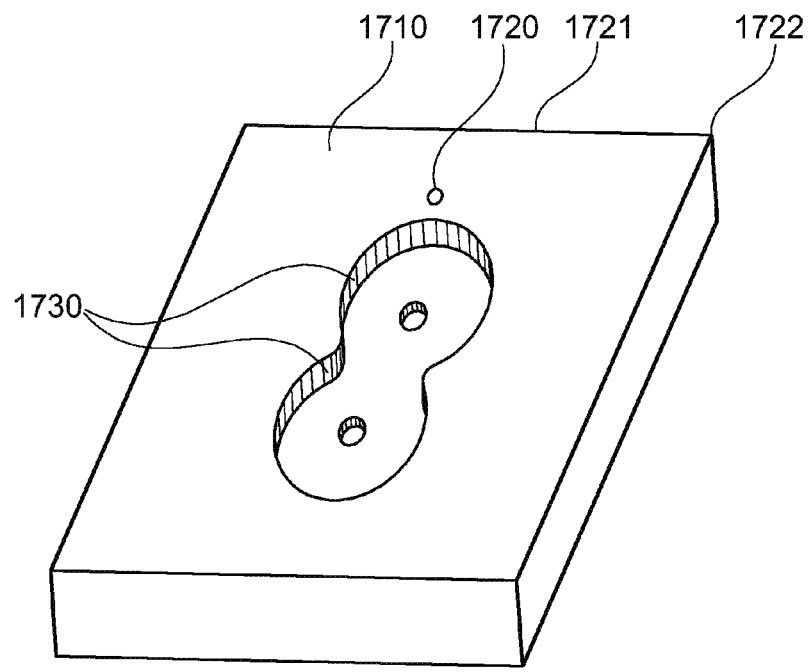
FIG. 17 shows a storage unit adapted for storing a medical implant comprising two circular shapes prior to inserting the medical implant in a recess made in a joint.
Figure 17:
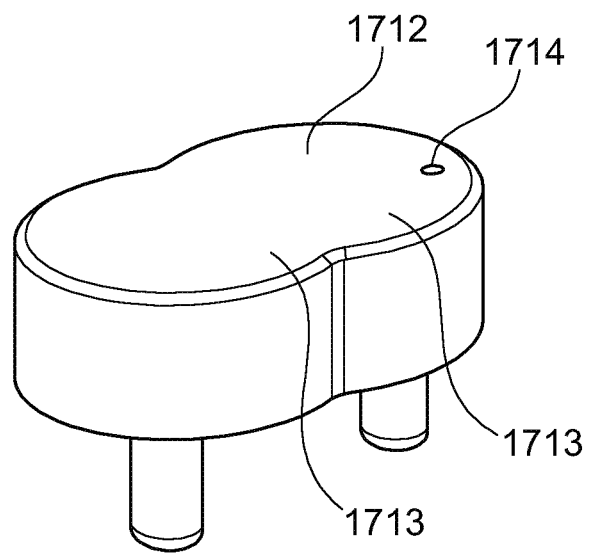

FIG. 17 shows a storage unit 1710 adapted for storing a medical implant comprising two circular shapes 1713 prior to inserting the medical implant 1712 in a recess made in a joint. The storage unit 1710 illustrated in FIG. 17 comprises a plurality of reference features in the form of a positioning mark 1720, an edge 1721 and a corner 1722.

The storage unit 1710 illustrated in FIG. 17 further comprises a mechanical recess structure 1730 adapted for holding and positioning the implant in a rotationally fixed position in the storage unit.

The plurality of reference features 1720, 1721, 1722 of the storage unit 1710 illustrated in FIG. 17 are adapted to be used for rotationally positioning an implant 1712 comprising the two circular shapes 1713 in the storage unit 1710 in that a positioning mark 1714 on one of the circular shapes 1713 is used for rotationally positioning the implant 1712 in relation to the plurality of reference features. The implant is then placed in the storage unit 1710 by directing the implant positioning mark 1714 on the surface of the implant in relation to at least one of the plurality of reference features of the storage unit, e.g. the implant positioning mark 1714 may be directed in the direction of the positioning mark 1720 on the upper surface of the storage unit 1710.

The invention claimed is:

1. A method for designing an implant, comprising:
designing a contour curvature of the implant so that an articulating surface of the implant is designed to correspond to a simulated healthy articulating surface of a damaged articulating surface of a joint;
designing at least two substantially circular shapes such that each of said substantially circular shapes is partly overlapping at least one other substantially circular shape, wherein a diameter of each substantially circular shape and a distance between axes of substantially circular shapes are selected based on one or more images taken with MRI or CT-scanning of a damaged cartilage surface of the joint; and
providing at least one positioning mark on at least one of said at least two substantially circular shapes such that said at least one positioning mark is designed to be used for determining the orientation in which the implant is to be placed in a recess made in a damaged articulating surface of a joint.

2. The method according to claim 1, further comprising providing at least one of said at least one positioning mark on the articulating surface of one of said at least two substantially circular shapes.

3. The method according to claim 1, further comprising providing said at least one positioning mark on the side edge of one of said at least two substantially circular shapes.

4. The method according to claim 1, further comprising:
designing the contour curvature of the implant so that the articulating surface of the implant corresponds to a simulated healthy articulating surface reconstructed from a 3D model based on one or more images taken with MRI or CT-scanning of a damaged articular surface.

5. The method according to claim 1, further comprising:
designing the contour curvature of the implant to be patient customized in that the articulating surface of the implant corresponds to a simulated healthy articulating surface reconstructed from a 3D model based on one or more images taken with MRI or CT-scanning of the damaged articulating surface in which the implant is to be placed in a recess.

6. The method according to claim 1, further comprising:
designing the shape and size of the implant dependent on the size and shape of the damage in the articulating surface and dependent on the curvature of the simulated healthy contour of the articulating surface in the area substantially coinciding with the damage; and
designing the positioning mark to point out the same direction, or joint axis, as at least one of a mark made, or to be made, on the side of a recess in a damaged articulating surface of a joint and a positioning mark on a guide tool to be used for facilitating placement of said implant in the recess.

\* \* \* \* \*